(12) United States Patent
Mihashi et al.

(10) Patent No.: US 6,905,209 B2
(45) Date of Patent: Jun. 14, 2005

(54) OPTICAL CHARACTERISTICS MEASURING DEVICE

(75) Inventors: Toshifumi Mihashi, Tokyo (JP); Yoko Hirohara, Tokyo (JP); Naoyuki Maeda, Osaka (JP)

(73) Assignee: Kabushiki Kaisha Topcon, Tokyo (JP)

(*) Notice: Subject to any disclaimer, the term of this patent is extended or adjusted under 35 U.S.C. 154(b) by 82 days.

(21) Appl. No.: 10/399,612

(22) PCT Filed: Oct. 16, 2001

(86) PCT No.: PCT/JP01/09084

§ 371 (c)(1), (2), (4) Date: May 16, 2003

(87) PCT Pub. No.: WO02/32299

PCT Pub. Date: Apr. 25, 2002

(65) Prior Publication Data

US 2003/0189690 A1 Oct. 9, 2003

(30) Foreign Application Priority Data

| Oct. 18, 2000 | (JP) | 2000-318559 |
| Nov. 17, 2000 | (JP) | 2000-350659 |
| Nov. 17, 2000 | (JP) | 2000-351796 |
| Apr. 18, 2001 | (JP) | 2001-119086 |

(51) Int. Cl.[7] .................................................. A61B 3/10
(52) U.S. Cl. .................................................... 351/221
(58) Field of Search ................................. 351/205, 206, 351/211, 212, 221, 246, 247

(56) References Cited

U.S. PATENT DOCUMENTS

| 5,500,697 A | * 3/1996 | Fujieda ..................... 351/212 |
| 5,841,511 A | 11/1998 | D-Souza et al. |
| 6,042,233 A | 3/2000 | Mihashi et al. |

FOREIGN PATENT DOCUMENTS

| JP | 8-504108 A | 5/1996 |
| JP | 8-215149 A | 8/1996 |
| JP | 9-053917 A | 2/1997 |
| JP | 2691268 B2 | 9/1997 |
| JP | 10-216092 A | 8/1998 |
| JP | 10-276988 A | 10/1998 |
| JP | 10-305013 A | 11/1998 |
| JP | 11-028188 A | 2/1999 |
| JP | 11-137520 A | 5/1999 |
| JP | 11-137522 A | 5/1999 |

OTHER PUBLICATIONS

U.S. Appl. No. 10/399,611, filed Apr. 18, 2003, Mihashi et al.

* cited by examiner

Primary Examiner—George Manuel
(74) Attorney, Agent, or Firm—Foley & Lardner LLP

(57) ABSTRACT

Measurement data (measured results) obtained under a plurality of conditions and image data and/or numerical data corresponding to the measured results are displayed collectively or selectively. An optical characteristics measuring device (100) measures/displays, for example, the optical characteristics of an eye to be measured (60) as an object. A first lighting optical system (10) includes a first light source (11) for applying an optical flux of a specified pattern to the eye to be measured (60). A first light receiving optical system (20) includes a first light receiving unit (23) for receiving light reflected from the eye (60). A light transmitting/receiving optical system (30) mainly conducts an alignment adjustment, and includes a second light receiving unit (35) for receiving light reflected from the eye (60). A common optical system (40) is disposed on the optical axis of a light flux emitted from the first lighting optical system (10), and is commonly included in the first lighting.

26 Claims, 28 Drawing Sheets

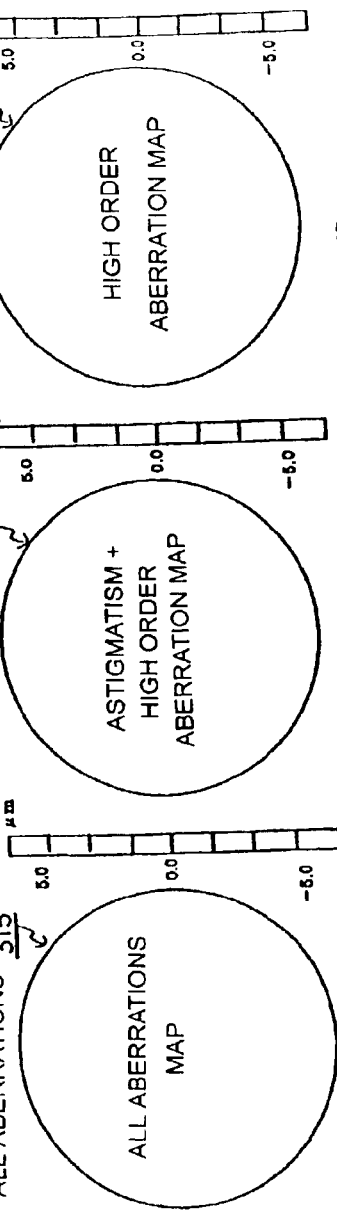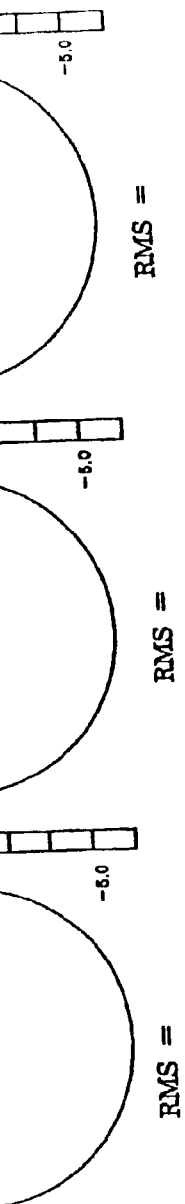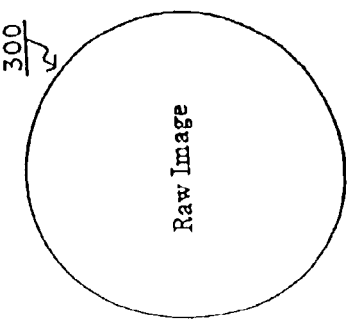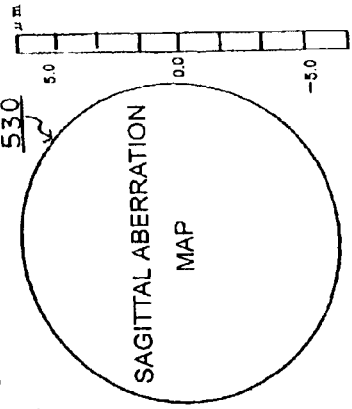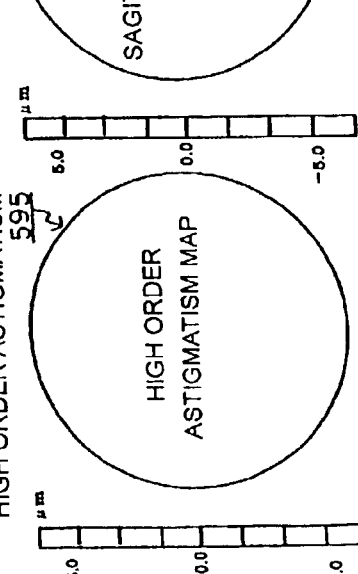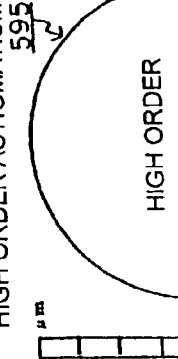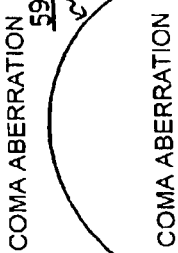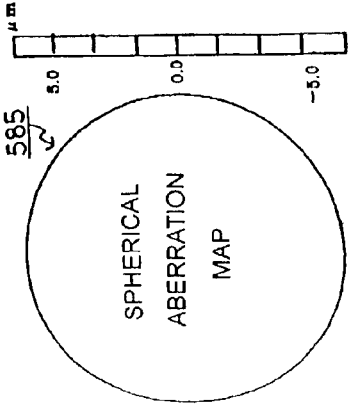
FIG. 17

600

| NAME | ZERNIKE ABERRATION COEFFICIENT | DIRECTION Ax (ccw FROM x AXIS) | RMS |
|---|---|---|---|
| 601 THIRD-ORDER SPHERICAL ABERRATION | $C_{42}$ | | $\frac{1}{\sqrt{5}}C_{42}$ |
| 602 FIFTH-ORDER SPHERICAL ABERRATION | $C_{63}$ | | $\frac{1}{\sqrt{7}}C_{63}$ |
| 603 SEVENTH-ORDER SPHERICAL ABERRATION | $C_{84}$ | | $\frac{1}{3}C_{84}$ |
| 604 THIRD-ORDER COMA ABERRATION | $\sqrt{C_{31}^2+C_{32}^2}$ | $\tan^{-1}(-\frac{C_{31}}{C_{32}})+90°$ | $\frac{1}{2\sqrt{2}}\sqrt{C_{31}^2+C_{32}^2}$ |
| 605 SAGITTAL ABERRATION | $\sqrt{C_{30}^2+C_{33}^2}$ | $\frac{1}{3}\tan^{-1}(-\frac{C_{30}}{C_{33}})+90°$ | $\frac{1}{2\sqrt{2}}\sqrt{C_{30}^2+C_{33}^2}$ |
| 606 FIFTH-ORDER COMA ABERRATION | $\sqrt{C_{52}^2+C_{53}^2}$ | $\tan^{-1}(-\frac{C_{52}}{C_{53}})+90°$ | $\frac{1}{2\sqrt{3}}\sqrt{C_{52}^2+C_{53}^2}$ |
| 607 THIRD-ORDER ASTIGMATISM | $\sqrt{C_{20}^2+C_{22}^2}$ | $\frac{1}{2}\tan^{-1}(-\frac{C_{20}}{C_{22}})+90°$ | $\frac{1}{\sqrt{6}}\sqrt{C_{20}^2+C_{22}^2}$ |
| 608 FIFTH-ORDER ASTIGMATISM | $\sqrt{C_{41}^2+C_{43}^2}$ | $\frac{1}{2}\tan^{-1}(-\frac{C_{41}}{C_{43}})+90°$ | $\frac{1}{\sqrt{10}}\sqrt{C_{41}^2+C_{43}^2}$ |

FIG. 18

$$\begin{bmatrix} i & j & \\ 0 & 0 & 1 \\ 1 & 0 & r\sin(t) \\ 1 & 1 & \cos(t)\,r \\ 2 & 0 & r^2\sin(2t) \\ 2 & 1 & 2r^2-1 \\ 2 & 2 & r^2\cos(2t) \\ 3 & 0 & r^3\sin(3t) \\ 3 & 1 & (3r^3-2r)\sin(t) \\ 3 & 2 & (3r^3-2r)\cos(t) \\ 3 & 3 & r^3\cos(3t) \\ 4 & 0 & r^4\sin(4t) \\ 4 & 1 & (4r^4-3r^2)\sin(2t) \\ 4 & 2 & 6r^4-6r^2+1 \\ 4 & 3 & (4r^4-3r^2)\cos(2t) \\ 4 & 4 & r^4\cos(4t) \\ 5 & 0 & r^5\sin(5t) \\ 5 & 1 & (5r^5-4r^3)\sin(3t) \\ 5 & 2 & (10r^5-12r^3+3r)\sin(t) \\ 5 & 3 & (10r^5-12r^3+3r)\cos(t) \\ 5 & 4 & (5r^5-4r^3)\cos(3t) \\ 5 & 5 & r^5\cos(5t) \\ 6 & 0 & r^6\sin(6t) \\ 6 & 1 & (6r^6-5r^4)\sin(4t) \\ 6 & 2 & (15r^6-20r^4+6r^2)\sin(2t) \\ 6 & 3 & 20r^6-30r^4+12r^2-1 \\ 6 & 4 & (15r^6-20r^4+6r^2)\cos(2t) \\ 6 & 5 & (6r^6-5r^4)\cos(4t) \\ 6 & 6 & r^6\cos(6t) \end{bmatrix}$$

FIG. 19

$$\begin{bmatrix}
i & j & \\
0 & 0 & 1 \\
1 & 0 & y \\
1 & 1 & x \\
2 & 0 & 2yx \\
2 & 1 & 2x^2 + 2y^2 - 1 \\
2 & 2 & x^2 - y^2 \\
3 & 0 & 3yx^2 - y^3 \\
3 & 1 & 3yx^2 + 3y^3 - 2y \\
3 & 2 & 3x^3 + 3xy^2 - 2x \\
3 & 3 & x^3 - 3xy^2 \\
4 & 0 & 4yx^3 - 4y^3 x \\
4 & 1 & 8yx^3 + 8y^3 x - 6yx \\
4 & 2 & 6x^4 + 12x^2 y^2 + 6y^4 - 6x^2 - 6y^2 + 1 \\
4 & 3 & 4x^4 - 4y^4 - 3x^2 + 3y^2 \\
4 & 4 & x^4 - 6x^2 y^2 + y^4 \\
5 & 0 & 5yx^4 - 10y^3 x^2 + y^5 \\
5 & 1 & 15yx^4 + 10y^3 x^2 - 5y^5 - 12yx^2 + 4y^3 \\
5 & 2 & 10yx^4 + 20y^3 x^2 + 10y^5 - 12yx^2 - 12y^3 + 3y \\
5 & 3 & 10x^5 + 20x^3 y^2 + 10xy^4 - 12x^3 - 12xy^2 + 3x \\
5 & 4 & 5x^5 - 10x^3 y^2 - 15xy^4 - 4x^3 + 12xy^2 \\
5 & 5 & x^5 - 10x^3 y^2 + 5xy^4 \\
6 & 0 & 6yx^5 - 20y^3 x^3 + 6y^5 x \\
6 & 1 & 24yx^5 - 24y^5 x - 20yx^3 + 20y^3 x \\
6 & 2 & 30yx^5 + 60y^3 x^3 + 30y^5 x - 40yx^3 - 40y^3 x + 12yx \\
6 & 3 & 20x^6 + 60x^4 y^2 + 60x^2 y^4 + 20y^6 - 30x^4 - 60x^2 y^2 - 30y^4 + 12x^2 + 12y^2 - 1 \\
6 & 4 & 15x^6 + 15x^4 y^2 - 15x^2 y^4 - 15y^6 - 20x^4 + 20y^4 + 6x^2 - 6y^2 \\
6 & 5 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6
\end{bmatrix}$$

FIG. 20

FIG. 22 CORNEA + EYEBALL POWER MAP

OCULAR OPTICAL SYSTEM REFRACTIVE POWER MAP + ABERRATION MAP

FIG. 24
OCULAR INTERNAL OPTICS REFRACTIVE POWER MAP    OD    MITSUKO TOKYO    MARCH 2, 2000    8:04 A.M.

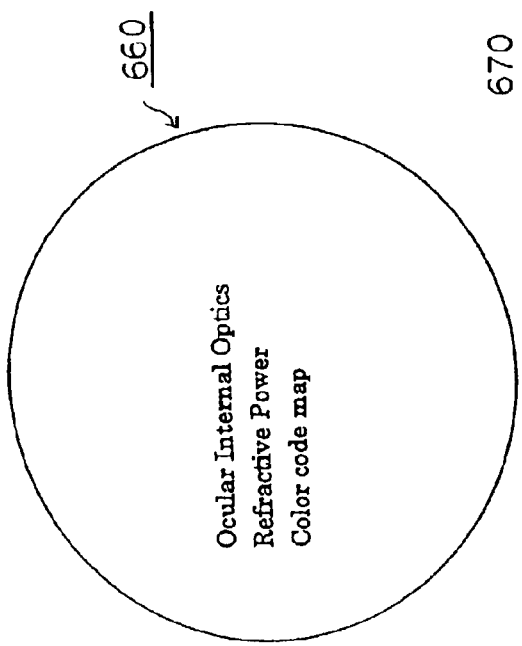

660: Ocular Internal Optics Refractive Power Color code map

670:

| Zernike COEFFICIENTS (RMS in Diopter) | Ocular Internal Optics Refractive power analysis | |
|---|---|---|
| | PHOTOPIC TIME (φ3mm) | SCOTOPIC TIME (φ7mm) |
| MEAN power | | |
| SPHERICAL ABERRATION | | |
| COMA ABERRATION | | |
| ASTIGMATISM | | |
| SAGITTAL ABERRATION | | |
| RESIDUAL ABERRATION | | |
| Total | | |

OPTICAL CHARACTERISTICS MEASURING DEVICE

BACKGROUND OF THE INVENTION

The present invention relates to an optical characteristic measuring apparatus, and particularly to an optical characteristic measuring apparatus for graphically displaying various data obtained by measurement under plural conditions.

In recent years, the variety of optical instruments used for medicine is very wide. Especially in ophthalmology, this optical instrument is in widespread use as an optical characteristic measuring apparatus for examining ocular functions such as ocular refraction or adjustment, and the inside of an eyeball. With respect to measurement results of these various tests, it is important that a patient's eye to be measured as a test object is placed under what measurement conditions. For example, since the pupil of an eye becomes small in a bright place, and becomes large in a dark place, it is necessary to also consider luminous intensity as the measurement condition, and further, a measurement range of the eye to be measured is also important.

Besides, the shapes of a retina, a cornea and other parts of an eye are often peculiar to a patient, and in order for an eye doctor or the like to quickly perform diagnosis of the patient's eye to be measured, it is desirable that various data relating to the respective parts of the eye to be measured are collectively displayed or desired data are selected and displayed. By this, the eye doctor or the like can intelligibly explain various diagnoses (observations) to the patient.

Besides, the various kinds of data correspond to ophthalmic optical characteristics, and are divided into, for example, numerical data and image data (graphic data), and with respect to these numerical data and graphic data, it is necessary that various images photographed by image pickup means (for example, CCD) of an optical instrument are processed or synthesized to bring them into a state where they are visually easy to see. Further, it is necessary that measured results of various data, measurement data, and numerical data corresponding to the measured results are displayed under plural conditions.

SUMMARY OF THE INVENTION

However, in the conventional optical characteristic measuring apparatus, it is presumed that it is difficult to collectively or selectively display various data obtained under plural conditions, such as measurement data (measured results), and image data and numerical data corresponding to the measured results, and to make them visually easy to see.

In view of the above, an object of the present invention is to provide an optical characteristic measuring apparatus which collectively or selectively displays measurement data (measured results) obtained under plural conditions, image data and/or numerical data corresponding to the measured results.

Besides, another object of the invention is to provide an optical characteristic measuring apparatus which collectively or selectively displays, with respect to the whole, cornea, interocular parts or the like of an eye to be measured, measurement data (measured results), image data and/or numerical data corresponding to the measured results by using a graphic display or the like.

First solving means of the invention provides an optical characteristic measuring apparatus comprising an illumination optical system including a light source section for applying a light flux of a predetermined pattern to an eye to be measured, a light receiving optical system including a light receiving section for receiving reflected light from the eye to be measured, a calculation section for calculating measured results for a graphic display based on received optical signals indicating measurement data from the light receiving section, and a display section for graphically displaying the measurement data based on the received optical signals and the measured results obtained by the calculation section.

Second solving means of the invention provides an optical characteristic measuring apparatus comprising an illumination optical system including a light source section for applying a light flux of a predetermined pattern to an eye to be measured, a light receiving optical system including a light receiving section for receiving reflected light from the eye to be measured, a calculation section for calculating, based on received optical signals indicating measurement data from the light receiving section, optical characteristics of the eye to be measured in a form of refraction or power as the measurement data, and a display section for graphically displaying an optical refraction distribution or a power map in accordance with the measurement data obtained by the calculation section.

BRIEF DESCRIPTION OF THE DRAWINGS

FIG. 17 is an explanatory view showing an eighth display example graphically displayed on the display section 230.

FIG. 18 is a view showing an expressive form 600 of respective aberrations with Zernike coefficients Cij.

FIG. 19 is a view showing classification of Zernike polynomials Zij into aberrations in polar display.

FIG. 20 is a view showing classification of Zernike polynomials Zij into aberrations in X-Y coordinate display.

FIG. 24 is an explanatory view showing an eleventh display example graphically displayed on the display section 230.

DETAILED DESCRIPTION OF THE PREFERRED EMBODIMENTS

Hereinafter, embodiments of the present invention will be described in detail with reference to the drawings.

Figure 1:
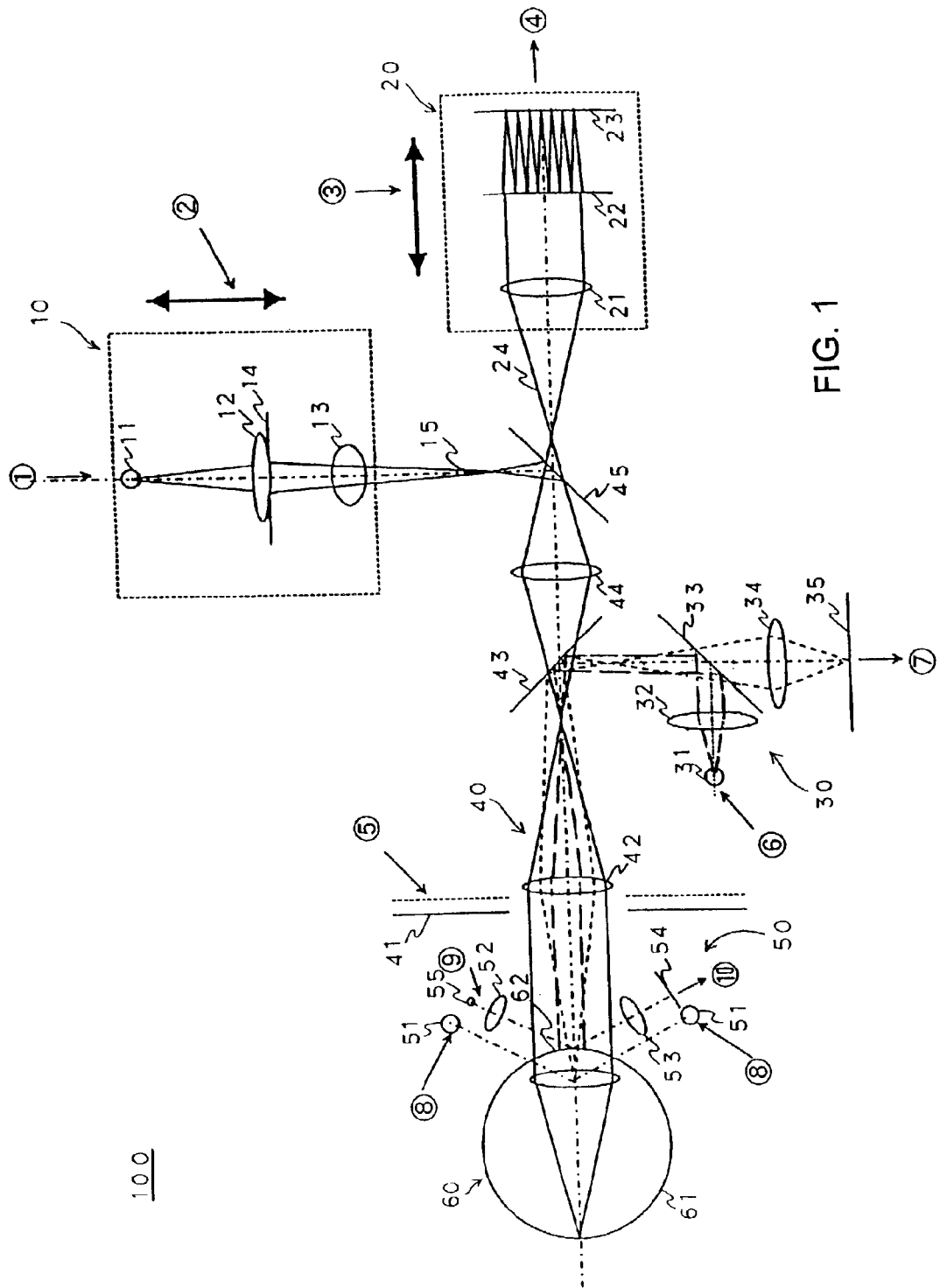
FIG. 1 is a view showing a schematic optical system of an optical characteristic measuring apparatus 100 of the invention.

FIG. 1 is a view schematically showing an optical system 100 of an ophthalmic optical characteristic measuring apparatus of the invention.

The optical system 100 of the ophthalmic optical characteristic measuring apparatus is, for example, an apparatus for measuring the optical characteristics of an eye 60 to be measured as an object, and includes a first illumination optical system 10, a first light receiving optical system 20, a second light receiving optical system 30, a common optical system 40, an adjusting optical system 50, a second illumination optical system 70, and a second light sending optical system 80. Incidentally, with respect to the eye 60 to be measured, a retina 61 and a cornea 62 are shown in the drawing.

The first illumination optical system 10 includes, for example, a first light source section 11 for emitting a light flux of a first wavelength, and a condensing lens 12, and is for illuminating a minute region on the retina (eyeground) 61 of the eye 60 to be measured by the light flux from the first light source section 11 so that the illumination conditions can be suitably set. Incidentally, here, as an example, the first wavelength of the light flux for illumination emitted from the first light source section 11 is a wavelength of an infrared range (for example, 780 nm, etc.).

Besides, it is desirable that the first light source section 11 has a large spatial coherence and a small temporal coherence. Here, the first light source section 11 is, for example, a super luminescence diode (SLD), and a point light source having high luminance can be obtained. Incidentally, the first light source section 11 is not limited to the SLD, and for example, even a laser having a large spatial coherence and a large temporal coherence can be used by inserting a rotational diffusion plate to suitably lower the temporal coherence. Further, even an LED having a small spatial coherence and a small temporal coherence can be used by, if light quantity is sufficient, inserting a pinhole or the like at the position of a light source of a light path. A bad influence on a Hartmann image by reflection characteristics of a coherence eyeground can be removed by inserting a rotation D prism at a pupil conjugated position in the apparatus and by scanning an illuminated minute region of the eyeground.

The first light receiving optical system 20 includes, for example, a collimate lens 21, a Hartmann plate 22 as a conversion member for converting a part of a light flux (first light flux) reflected and returned from the retina 61 of the eye 60 to be measured into at least 17 beams, and a first light receiving section 23 for receiving the plural beams converted by the Hartmann plate 22, and is for guiding the first light flux to the first light receiving section 23. Here, a CCD with low lead-out noise is adopted for the first light receiving section 23, and as the CCD, a suitable type one, for example, a general low noise type one or a cooling CCD of 2000*2000 elements for measurement can be applied.

A light transmitting/receiving optical system 30 mainly performs an alignment adjustment described later, includes a second light source section 31 for emitting a light flux of a second wavelength, condensing lenses 32 and 34, a beam splitter 33, and a second light receiving section 35, is for guiding a light flux (second light flux) reflected and returned from the cornea 62 of the eye 60 to be measured to the second light receiving section, and mainly performs the alignment adjustment. Besides, the second wavelength of the light flux emitted from the second light source section 31 is different from, for example, the first wavelength (here, 780 nm), and a long wavelength can be selected (for example, 940 nm).

A common optical system 40 is disposed on the optical axis of the light flux emitted from the first illumination optical system 10, and can be commonly included in the first illumination optical system 10, the first light receiving optical system 20, and the light transmitting/receiving optical system 30, and includes, for example, a placido ring 41, an afocal lens 42, beam splitters 43 and 45, and a condensing lens 44. The placido ring 41 projects an index of a pattern made of plural co-axial rings after alignment adjustment described later is completed. The beam splitter 43 is formed of a mirror (for example, a dichroic mirror) which sends (reflects) the light of the wavelength of the second light source section 31 to the eye 60 to be measured, reflects the second light flux reflected and returned from the cornea 62 of the eye 60 to be measured, and allows the wavelength of the first light source section 11 to pass through. The beam splitter 45 is formed of a mirror (for example, polarization beam splitter) which sends (reflects) the light of the wavelength of the first light source section 11 to the eye 60 to be measured, and allows the first light flux reflected and returned from the retina 61 of the eye 60 to be measured to pass through. The beam splitters 43 and 45 prevent the first and the second light fluxes from mutually entering other optical systems to generate noise.

The adjusting optical system 50 mainly performs, for example, a working distance adjustment described later, and includes a third light source section 51, a fourth light source section 55, condensing lenses 52 and 53, and a third light receiving section 54.

Next, the alignment adjustment will be described. The alignment adjustment is mainly carried out by the second light receiving optical system 30 and the second light sending optical system 80.

First, the light flux from the second light source section 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux as if it is emitted from a point of ½ of the radius of curvature of the cornea 62. This divergent light source is received as a spot image by the second light receiving section 35 through the afocal lens 42, the beam splitters 43 and 33, and the condensing lens 34.

Here, in the case where the spot image on the second light receiving section 35 is deviated from the light axis, the body of the ophthalmic optical characteristic measuring apparatus is moved and adjusted vertically and horizontally to make the spot image coincident with the light axis. When the spot image coincides with the optical axis in this way, the alignment adjustment is completed. Incidentally, when the cornea 62 of the eye 60 to be measured is illuminated with a third light source section 51, an image of the eye 60 to be measured obtained by this illumination is formed on the second light receiving section 35, and accordingly, the alignment adjustment may be made such that this image is used to make the pupil center coincident with the optical axis.

Next, the working distance adjustment will be described. The working distance adjustment is carried out mainly by the adjusting optical system 50.

First, the working distance adjustment is carried out in such a manner that the parallel light flux in the vicinity of the optical axis emitted from the fourth light source section 55 is illuminated to the eye 60 to be measured, and the light reflected from this eye 60 to be measured is received by the third light receiving section 54 through the condensing lenses 52 and 53. In the case where the eye 60 to be measured is within a suitable working distance, a spot image from the fourth light source section 55 is formed on the optical axis of the third light receiving section 54. On the other hand, in the case where the eye 60 to be measured is outside the suitable working distance in front and rear, the spot image from the fourth light source 55 is formed above or below the optical axis of the third light receiving section 54. Incidentally, since it is sufficient if the third light receiving section 54 can detect the change of the light flux position on the plane including the fourth light source section 55, the optical axis, and the third light receiving section 54, for example, a one-dimensional CCD disposed on this plane, a position sensing device (PSD) or the like can be applied.

Next, the positional relation between the first illumination optical system 10 and the first light receiving optical system 20 will be roughly described.

The beam splitter 45 is inserted in the first light receiving optical system 20, and by this beam splitter 45, the light from the first illumination optical system 10 is sent to the eye 60 to be measured, and the reflected light from the eye 60 to be measured is transmitted. The first light receiving section 23 included in the first light receiving optical system 20 receives the light transmitted through the Hartmann plate 22 as the conversion member and generates a received light signal.

The first light source section 11 and the retina 61 of the eye 60 to be measured form a conjugate relation. The retina 61 of the eye 60 to be measured and the first light receiving section 23 are conjugate with each other. The Hartmann plate 22 and the pupil of the eye 60 to be measured form a conjugate relation. The first light receiving optical system 20, the cornea 62 and pupil of the eye 60 to be measured, and Hartmann plate 22 form a conjugate relation. That is, the front side focus of the afocal lens 42 is substantially coincident with the pupil of the eye 60 to be measured.

The first illumination optical system 10 and the first light receiving optical system 20 are moved together so that on the assumption that the light flux from the first light source 11 is reflected at the condensed point, a signal peak by the reflected light at the first light receiving section 23 becomes maximum. Specifically, the first illumination optical system 10 and the first light receiving optical system 20 move in the direction that the signal peak at the first light receiving section 23 becomes large, and stop at the position where the signal peak becomes maximum. By this, the light flux from the first light source section 11 is condensed on the eye 60 to be measured.

The lens 12 converts the diffused light of the light source 11 into parallel light. A diaphragm 14 is put at a position optically conjugate with the pupil of the eye or the Hartmann plate 22. In the diaphragm 14, its diameter is smaller than the effective range of the Hartmann plate 22, and so-called single path aberration measurement (a method in which aberration of an eye influences only the light receiving side) is established. A lens 13 is disposed such that an eyeground conjugate point of a real light beam is at the front side focal position to satisfy the above, and further, the rear side focal position is coincident with the diaphragm 14 to satisfy the conjugate relation to the pupil of the eye.

After a light beam 15 comes to have an optical path common to a light beam 24 by the beam splitter 45, it approximately advances in the same way as the light beam 24. At the time of single path measurement, the diameters of the respective light beams are different from each other, and the beam diameter of the light beam 15 is set to be rather thinner than the light beam 24. Specifically, the beam diameter of the light beam 15 is, for example, about 1 mm at the position of the pupil of the eye, and the beam diameter of the light beam 24 becomes about 7 mm (incidentally, in the drawing, the light beam 15 from the beam splitter 45 to the eyeground 61 is omitted.

Next, the Hartmann plate 22 as the conversion member will be described.

The Hartmann plate 22 included in the first light receiving optical system 20 is a wavefront conversion member for converting a reflected light flux into plural beams. Here, plural micro Fresnel lenses disposed in the plane orthogonal to the optical axis are applied for the Hartmann plate 22. In general, with respect to a measurement object (the eye 60 to be measured), in order to measure a spherical component of the eye 60 to be measured, third astigmatism, and the Zernike's third and forth order aberration, it is necessary to make a measurement with at least 17 beams through the eye 60 to be measured.

The micro Fresnel lens is an optical element, and includes, for example, rings of height pitch for each wavelength and blades optimized for emission parallel with condensing point. The micro Fresnel lens here is provided with light path length differences of eight levels in which a semiconductor minute working technique is applied, and achieves a high condensing rate (for example, 98%).

Besides, the reflected light from the retina 61 of the eye 60 to be measured passes through the afocal lens 42 and the collimate lens 21, and is condensed on the first light receiving section 23 through the Hartmann plate 22 as its primary light. The Hartmann plate 22 may include a microlens section for performing a converging action and an opening for performing a transmission action for each of at least 17 divided regions. Accordingly, the Hartmann plate 22 includes a wavefront conversion member for converting the reflected light flux into at least 17 beams.

Figure 2:
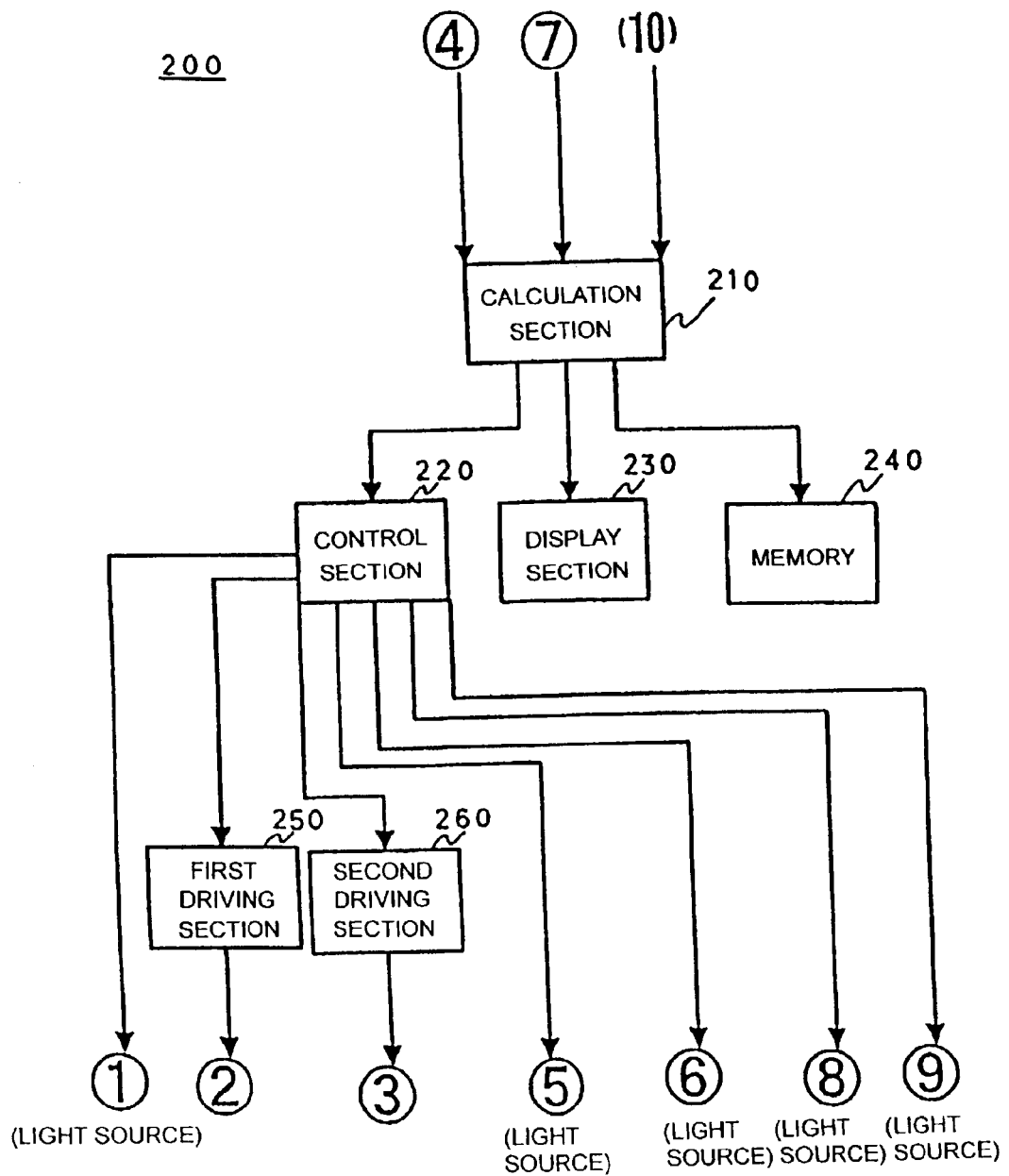
FIG. 2 is an electric system block diagram showing an electric structure of the optical characteristic measuring apparatus 100 of the invention.

FIG. 2 is a block diagram schematically showing an electric system of the optical characteristic measuring apparatus 100 of the invention.

The electric system of the optical characteristic measuring apparatus 100 includes, for example, a calculation section 210, a control section 220, a display section 230, a memory 240, a first driving section 250, and a second driving section 260, the calculation section 210 obtains the optical characteristics of the subject eye and the corneal shape of the subject eye on the basis of the first and the second signals selected by the input section 270. The calculation section 210 receives a received light signal (first signal) ④ obtained from the first light receiving section 23, a received light signal (second signal) ⑦ obtained from the second light receiving section 35, and a received light signal ⑩ obtained from the third light receiving section 54, and calculates a coordinate origin, a coordinate axis, movement of a coordinate, rotation, ocular aberration, corneal aberration, Zernike coefficients, aberration coefficients, Strehl ratio, white light MTF, Landolt's ring pattern(The details are described later.), and the like. Further, the calculation section outputs signals corresponding to the calculation results to the control section 220 for controlling the whole of the electric driving system, the display section 230(Display examples are described later.), and the memory 240.

The control section 220 controls switching on and off of the first light source section 11 on the basis of the control signal from the calculation section 210, and controls the first driving section 250 and the second driving section 260. For example, on the basis of the signal corresponding to the calculation result in the calculation section 210, the control section outputs a signal ① to the first light source section 11, outputs a signal ⑤ to the placido's disc 71, outputs a signal ⑥ to the second light source section 31, outputs a signal ⑧ to the third light source section 51, outputs a signal ⑨ to the fourth light source section 55, and outputs signals to the first driving section 250 and the second driving section 260.

The first driving section 250 moves to the optical axis direction, for example, the whole of the first illumination optical system 10 on the basis of the received light signal ④ inputted to the calculation section 210 from the first light receiving section 23, outputs a signal ② to a not-shown suitable lens moving unit, and drives the lens moving unit. By this, the first driving section 250 can move and adjust the first illumination optical system 10.

The second driving section 260 moves to the optical axis direction, for example, the whole of the first light receiving optical system 20 on the basis of the received light signal ④ inputted to the calculation section 210 from the first light receiving section 23, and outputs a signal ③ to the not-shown suitable lens moving unit, and drives the lens moving unit. By this, the second driving section 260 can move and adjust the first light receiving optical system 20.

Figure 3:
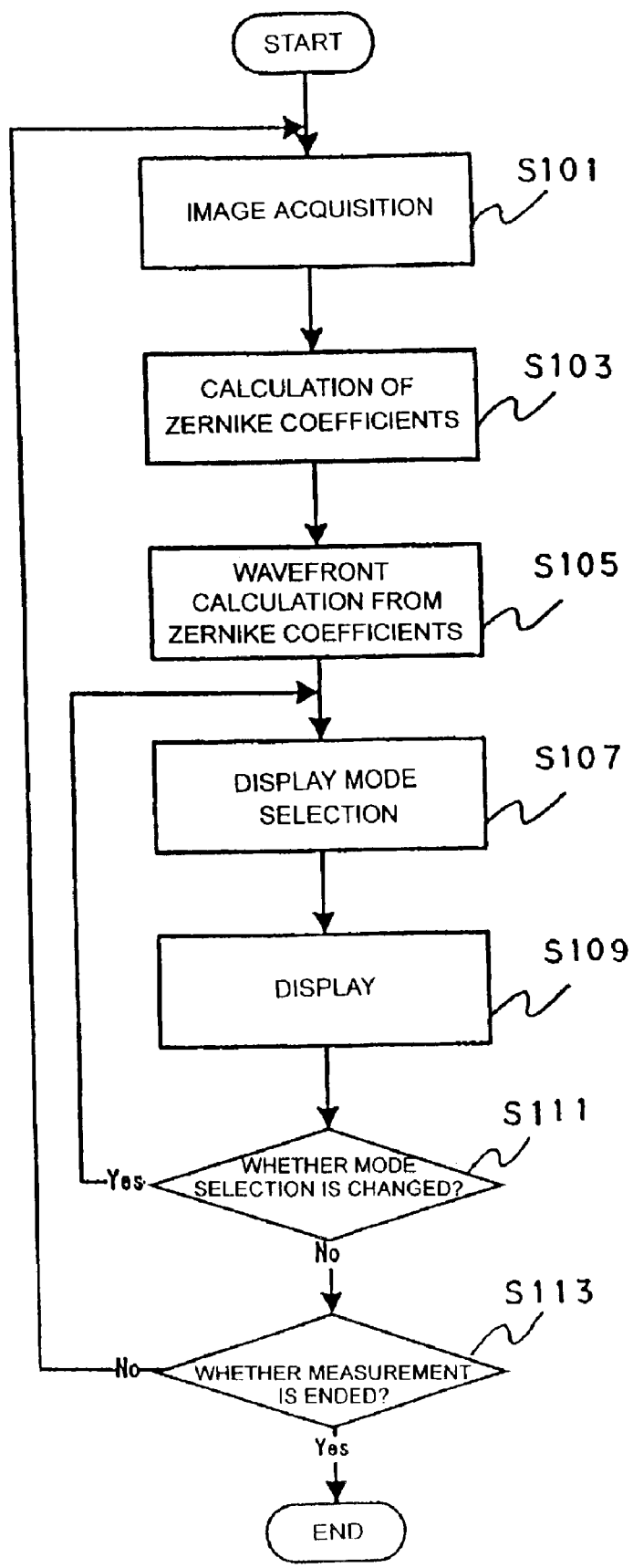
FIG. 3 is a flowchart of the optical characteristic measuring apparatus 100 of the invention.

FIG. 3 is a flowchart showing the operation of the optical characteristic measuring apparatus 100 of the invention. Incidentally, for convenience of explanation, the description of the flowchart here is made general, and a specific description will be given later.

First, a measurer starts measurement of the eye 60 to be measured as a measurement object, and the image (for example, Hartmann image, anterior eye image) from the first light receiving section 23 or the second light receiving section 35 is acquired (S101). Next, with respect to ocular aberration measurement, Zernike coefficients are calculated based on a distance between the Hartmann plate 22 and the first light receiving section 23 as numerical data concerning the Hartmann image at the step S101, and coordinates and the like, and with respect to corneal aberration measurement, Zernike coefficients are calculated based on a displacement amount by distortion of a placido ring image (S103). The wavefront or corneal aberration of the eye 60 to be measured is calculated based on the Zernike coefficients (S105).

Next, display mode selection is performed to determine how various data obtained from the steps S101 to S105 are displayed on the display section 230 (S107). Incidentally, the various data can be graphically displayed on the display section 230 collectively or selectively as the measurement data (measured results) obtained under plural conditions, the image data and/or numerical data corresponding to the measured results (the details will be described later). Besides, in accordance with the display mode selected at the step S107, various images and/or data are displayed on the display section 230 (S109).

Besides, in the case where a display example different from the display example at the step S109 is displayed on the display section 230, the display mode selection is again performed in order to change the display mode selection selected at the step S107 (S111). On the other hand, in the case where the display mode selection selected at the step S107 is not changed, it is judged whether or not the measurement is ended (S113). In the case where the measurement is not ended at the step S113, an image is again acquired. On the other hand, in the case where the measurement is to be ended, the measurement is ended.

Hereinafter, the processing of each of the foregoing steps will be described in detail.

(Concerning Step S101)
(Concerning the Image of the Eye 60 to be Measured, Which is Displayed on the Display Section 230)

This image is, for example, the so-called Hartmann image obtained by passaging through the opening bored in the Hartmann plate 22, and is a raw image photographed by the first light receiving section 23 to which CCDs as image pickup means are applied. Besides, the irradiation positions of the plural beams converted by the Hartmann plate 22 are changed in accordance with, for example, a deviation of alignment of the first light receiving optical system 20 with respect to the patent's eye 60 to be measured and higher order aberration components of the eye to be measured (corresponding to arrows indicated on the Hartmann image included in after-mentioned display examples).

(Concerning Steps S103 and S105)
(Concerning Zernike Coefficients Required when Ocular Aberration Map, Corneal Aberration Map, Bird's-Eye View, Ocular Aberration Display Section of Numerical Data, and Corneal Aberration Display Section are Displayed on the Display Section 230)

Here, a generally known method of calculating Zernike coefficients $C_{ij}$ by using Zernike polynomials $Z_{ij}$ (fixed values not changed depending on objects, and known here) will be described.

First, the Zernike coefficients $C_{ij}$ are important parameters for grasping the optical characteristics of the eye to be measured. The parameters become the operation principle of the calculation section 210 for obtaining the optical characteristics of the eye 60 to be measured based on, for example, the inclination angle of the light flux obtained by the first light receiving section 23 through the Hartmann plate 22.

The optical characteristic measuring apparatus 100 measures a higher order aberration (W(X,Y)) of the eye 60 to be measured. For this purpose, when the vertical and horizontal coordinates of the Hartmann plate 22 as the conversion member are made (X, Y), and the vertical and horizontal coordinates of the first light receiving section 23 are made (x, y), with respect to the higher order aberration W (X, Y) generally expressed by following numerical expression 3, the relations of following numerical expression 1 and numerical expression 2 are similarly established. That is, $$\frac{\partial W(X, Y)}{\partial X} = \frac{\Delta x}{f} \quad (1)$$

$$\frac{\partial W(X, Y)}{\partial Y} = \frac{\Delta y}{f} \quad (2)$$

Where, f: a distance between the Hartmann plate 22 and the first light receiving section 23.

$$W(X, Y) = \sum_{i=0}^{n} \sum_{j=0}^{i} c_{ij} Z_{ij}(X, Y) \quad (3)$$

Besides, the Zernike coefficients Cij are obtained by partially differentiating both sides of the numerical expression 3 with respect to the coordinates (X, Y) on the Hartmann plate 22.

Here, the Zernike polynomials Zij are expressed by following numerical expression 4 and numerical expression 5, and specifically, they are shown in FIGS. 19 and 20.

$$Z_{nm} = R_n^{n-2m}(r) \left\{ \begin{array}{c} \sin \\ \cos \end{array} \right\} \{(n - 2m)\theta\} \quad (4)$$

sin if $n - 2m > 0$
cos if $n - 2m \leq 0$ $$R_n^{n-2m}(r) = \sum_{S=0}^{m} (-1)^S \frac{(n-S)!}{S!(m-S)!(n-m-S)!} r^{n-2m} \quad (5)$$

Here, although the Zernike polynomials normalized by the absolute value are indicated, a polynomial normalized by RMS (root mean square), which is a standard in the OSA (Optical Society of America) and is different only in scalar times of coefficients, can also be used.

Besides, concrete values of the Zernike coefficients Cij can be obtained by minimizing the square error of the following numerical expression 6.

$$S(x) = \sum_{l=1}^{data\ number} \left[ \left\{ \frac{\partial W(X_l, Y_l)}{\partial X} - \frac{\Delta x_l}{f} \right\}^2 + \left\{ \frac{\partial W(X_l, Y_l)}{\partial Y} - \frac{\Delta y_l}{f} \right\}^2 \right] \quad (6)$$

(Concerning Steps S107 and S109)

Here, a description will be given of a display example in a case where measurement data (measured results) obtained under plural conditions, image data and/or numerical data corresponding to the measured results are collectively or selectively displayed on the display section 230.

First, in the display mode selection at the step S107, for example, the measurer can select a desired display example among first to thirteenth display examples described later. Incidentally, the measurer can selectively display respective elements included in the first to thirteenth display examples.

Here, for convenience of explanation, each of the elements included in the first to thirteenth display examples will be described.

(Concerning Aberration Coefficients Included in the Ocular Aberration Display Section Displayed on the Display Section 230)

In the case where the aberration components of the eye to be measured are converted into numbers as aberration coefficients (here, unit: μm), when they are Zernike coefficients (n=1, 2, 3, 4, 5, 6), and when RMS values (mean square error) of the aberration coefficients are made S1, S2, S3, S4, S5 and S6, $$S3 = \frac{1}{2\sqrt{2}} \sqrt{C_{30}^2 + C_{31}^2 + C_{32}^2 + C_{33}^2} \quad (7)$$

$$S4 = \frac{1}{\sqrt{10}} \sqrt{C_{40}^2 + C_{41}^2 + C_{42}^2 + C_{43}^2 + C_{44}^2}$$

$$S5 = \frac{1}{2\sqrt{3}} \sqrt{C_{50}^2 + C_{51}^2 + C_{52}^2 + C_{53}^2 + C_{54}^2 + C_{55}^2}$$

$$S6 = \frac{1}{\sqrt{14}} \sqrt{C_{60}^2 + C_{61}^2 + C_{62}^2 + 2C_{63}^2 + C_{64}^2 + C_{65}^2 + C_{66}^2}$$

$$S1 = \frac{1}{2} \sqrt{C_{10}^2 + C_{11}^2}$$

$$S2 = \frac{1}{\sqrt{6}} \sqrt{C_{20}^2 + 2C_{21}^2 + C_{22}}$$

$$S(3+5) = \sqrt{S3^2 + S5^2}$$

$$S(4+6) = \sqrt{S4^2 + S6^2}$$

$$S(3+4+5+6) = \sqrt{S3^2 + S4^2 + S5^2 + S6^2}$$

Where, S1 means a tilt, S3, S5 and S(3+5) become coma aberrations, and similarly, S2, S4, S6 and S(4+6) become spherical aberrations. Incidentally, normally, the aberration of S3 or higher except for S2 is called a high order aberration.

Next, classification of the high order aberration will be described.

The high order aberration is classified by, for example, a value of n of sin(nθ), cos(nθ) of the Zernike coefficients Cij (Zernike coefficients Cij include sine and cosine functions as expressed by the foregoing numerical expression 3 and numerical expression 4). Specifically, if n=0 (fold), it becomes the spherical aberration, if n=1 (fold), it becomes the coma aberration, and similarly, if n=2 (fold), it becomes astigmatism, and further, if n=3 (fold), it is classified into sagittal aberration.

Besides, symmetrical aberration (coma aberration) means fourth-order aberration+sixth-order aberration, and similarly, asymmetrical aberration (spherical aberration) means third-order aberration+fifth-order aberration. Incidentally, the order of the high order aberration is determined as the need arises, and in addition to the sixth order, for example, in the eighth order, third-order+fifth-order+seventh-order means coma aberration, and fourth-order+sixth-order+eighth-order means spherical aberration.

Next, a description will be given of a case where the respective aberrations are expressed using the Zernike coefficients Cij.

FIG. 18 is a view showing an expressive form 600 of the respective aberrations by the Zernike coefficients Cij.

The expressive form 600 of the respective aberrations is divided into items of, for example, a name of each aberration, a Zernike aberration coefficient, a direction Ax (for example, counterclockwise rotation from the X axis), and the foregoing RMS. Besides, the expressive form 600 of the respective aberrations includes, as shown in the drawing, an item 601 indicating the third-order spherical aberration, an item 602 indicating the fifth-order spherical aberration, an item 603 indicating the seventh-order spherical aberration, an item 604 indicating the third-order coma aberration, an item 605 indicating the sagittal aberration, an item 606 indicating the fifth-order coma aberration, an item 607 indicating the third astigmatism, and an item 608 indicating the fifth-order astigmatism. Incidentally, the respective aberrations are collectively or selectively displayed on the display section 230 as ocular and corneal aberration displays mainly in after-mentioned fifth to eighth display examples.

Next, a Power Map calculation method will be described.

First, a description will be given of a case where the obtained higher order aberration W(X, Y) is converted into a power display. Incidentally, this power display is mainly shown in after-mentioned ninth to thirteenth display examples.

Here, it is assumed that the position of the objective wavefront is expressed by X and Y, and in a section including the optical axis, a distance between a point where the normal of the wavefront at that position intersects with the optical axis and a position of the wavefront on the optical axis at that time is made $L_p$.

The power P at this time is made $1/L_p + 1/L_{eye}$. Here, $L_{eye}$ is a mean ocular axis length of an eye (for example, 0.017 (m)). Incidentally, a value measured by another apparatus may be inputted as this ocular axis length.

Besides, a power distribution at each position (r, t) of the wavefront is expressed by P(r, t). This power distribution P(r, t) corresponds to after-mentioned ocular refraction distribution (Ocular Refractive Power). Next, the higher order aberration W(X, Y) in the numerical expression 3 is replaced by the power distribution P(r, t), and the same processing as the above is performed, so that the Zernike coefficients Cij corresponding to the power distribution are obtained. Incidentally, here, as the Zernike polynomials Zij, those of the polar coordinate system shown in FIG. 19 are used. Here, the obtained Zernike coefficients are used to obtain the respective aberrations, such as the spherical aberration, the coma aberration and the astigmatism, corresponding to the power distribution.

Besides, in the case where the power distribution is approximated by the Zernike polynomials $Z_{ij}$, the kind of the aberration is classified and displayed as described below. Specifically, a classification is made as follows: at the 0th order, mean power; at a term without sin or cos, spherical aberration; at sin(t) or cos(t), coma aberration; at sin(2t) or cos(2t), astigmatism; and at sin(3t) or cos(3t), sagittal aberration.

Next, the Power Map of the front surface of the cornea is calculated from the reflected image from the front surface of the cornea of the placido ring.

Here, in the case where center positions of the respective rings are detected, the center position as reference is determined. For example, the center position of the innermost placido ring image is obtained, and is made to correspond to the respective rings. With respect to the center position of the innermost placido ring image, for example, it is assumed that the ring is elliptical, the respective points on the ring are functionally approximated to an expression of elliptic or the like by the method of least squares, and the center at that time is calculated. Besides, in the case where the positions of the respective points on the ring are detected, distances r from the center positions of the respective rings to the positions of the respective points on the respective rings are calculated.

Next, shape and Power calculation will be described.

First, it is assumed that the surface shape is a model curve f(r) at the distance r, and the sectional shape is calculated. Incidentally, for example, an aspherical surface or the like is used as the model curve. When the center position of the ring obtained at this time is made the original point, $$f(r) = \frac{cr^2}{1+\sqrt{1-pc^2r^2}} + A_2 r^2 + A_4 r^4 + \cdots \quad (8)$$

Where, p: Korenich coefficient, and c: radius of curvature at the center position.

Besides, the first derivation of this expression is $$\frac{df(r)}{dr} = \frac{cr}{\sqrt{1-pc^2r^2}} + 2A_2 r + 4A_4 r^3 + \cdots \quad (9)$$

Figure 21:
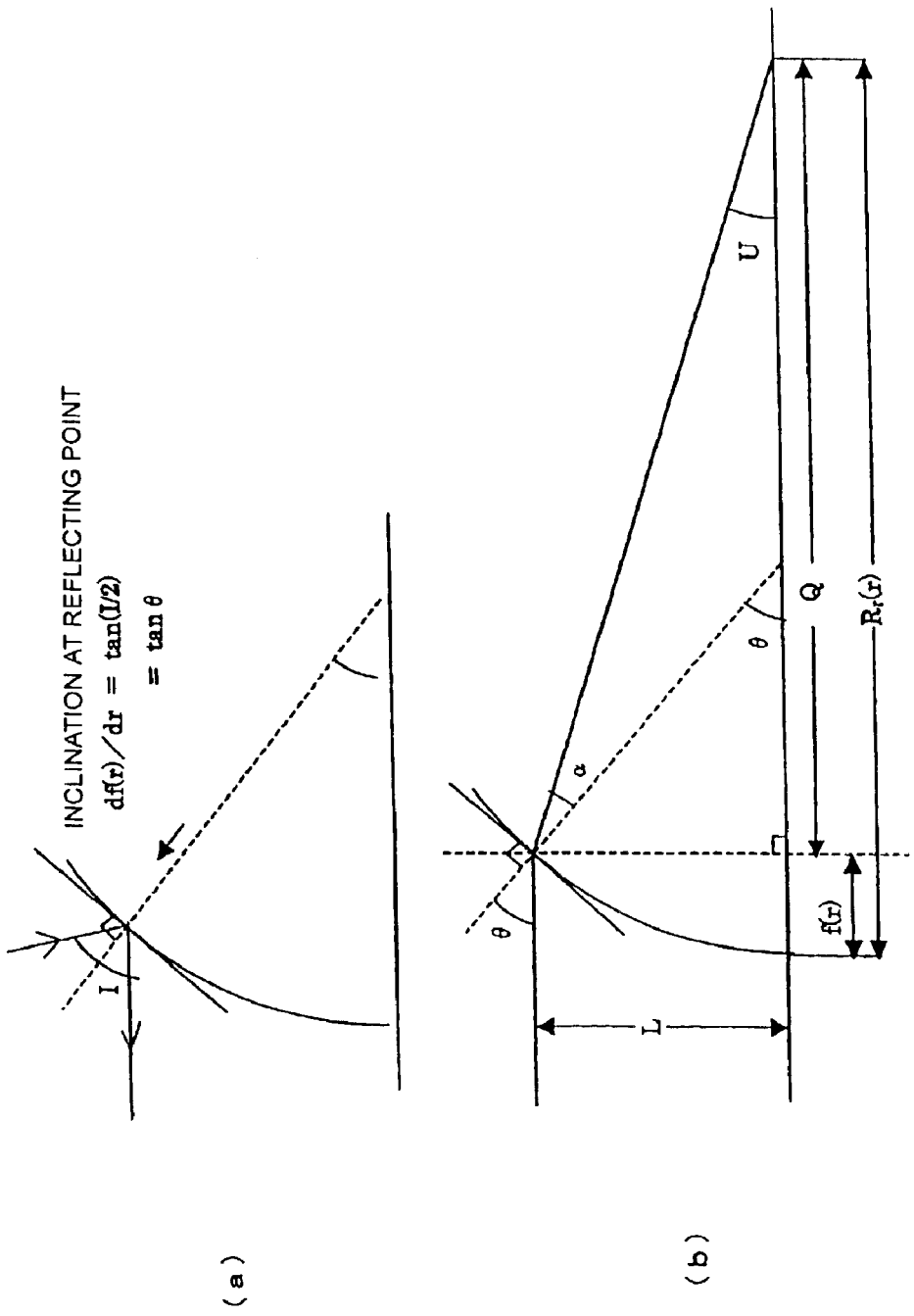
FIG. 21 is an explanatory view concerning shape and Power calculation.

FIG. 21(*a*) is an explanatory view (1) concerning the shape and the power calculation.

Here, an inclination at a reflection point is, for example, df(r)/dr=tan(1/2)=tan θ, and becomes a value independent on the radius of curvature at each point. Besides, r and df(r)/dr are functionally approximated to the expression of the first derivation by the method of least squares, and the respective coefficients A2, A4, . . . are obtained. By determining f(x) in this way, the radius of curvature $R_i(r)$ at each point on the section can be obtained. That is, $$R_i(r) = \frac{(1+\{f'(r)^2\})^{\frac{3}{2}}}{|f''(r)|} \quad (10)$$

Here, $f'(r)=d(fr)/dr$, $f''(r)=d^2f(r)/dr^2$.

Besides, from the numerical expression 10, Instantaneous Power $P_i$ is $$P_i(r)=n-1/R_i(r).$$

Where, n: corneal refraction.

Besides, at this time, a distance $R_a(r)$ between each point on the section and an intersection point of a normal of each point and a corneal optical axis is $$R_a(r) = \sqrt{1+\frac{1}{f'(r)^2}} \quad (11)$$

Besides, from the numerical expression 11, Axial Power $P_a(r)$ is obtained by $$P_a(r)=n-1/R_a(r)$$

FIG. 21(*b*) is an explanatory view (2) concerning the shape and the power calculation.

Here, when a light beam parallel to the corneal optical axis is incident on each point on the section, by the Snell's law, $$\sin θ=n \sin α→α=\sin^{-1}(1/n \sin θ) \; (θ=1/2).$$

Besides, an x component (optical axis direction) Q of a distance between each point on the section and the intersection point of the light beam and the corneal optical axis becomes $$Q=L/\tan \; U=\tan(θ-α).$$

By this, a distance $R_r(r)$ between the center position and the intersection point of the light beam and the corneal optical axis is obtained by $$Rr(r)=f(r)+Q.$$

From this $R_r(r)$, Refractive Power $P_r(r)$ becomes $$P_r(r)=n/R_r(r).$$

As stated above, in these three kinds of powers, the powers in one section are obtained. The bearing t of a radius vector r, and respective powers P(r, t) in all bearings t are obtained. Incidentally, t means the bearing of the radius vector r on the X-Y plane. Besides, the higher order aberration W(X, Y) in the foregoing numerical expression 3 is replaced by the power distribution P(r, t), and the same processing as the above is performed, so that the Zernike coefficients corresponding to the power distribution are obtained.

(Concerning White Light MTF Displayed on the Display Section 230)

Next, calculation of white light MTF (Modulation transfer function) will be described.

First, the MTF is an index indicating transmission characteristics of a spatial frequency and is widely used to express the performance of an optical system. In this MTF, it is possible to estimate appearance by obtaining, for example, the transmission characteristics for 0 to 100 sinusoidal concentration lattices per degree.

First, monochromatic MTF is calculated from the higher order aberration W (x, y). Incidentally, W(x, y) is an input value (measured value), and with respect to the corneal aberration, corneal higher order aberration obtained from the corneal shape can also be used.

A pupil function f(x, y) is obtained from the higher order aberration as follows.

$$f(x, y)=e^{ikw(x, y)}$$

Where, i: imaginary number, k: wave number vector ($2\pi/\lambda$).

Besides, this pupil function f(x, y) is subjected to Fourier transformation, so that an amplitude distribution U(u, v) of a point image is obtained.

$$U(u, v) = \int\int_{-\infty}^{\infty} f(x, y)\exp\left[-\frac{i}{R}\frac{2\pi}{\lambda}(ux+vy)\right]dxdy \quad (12)$$

Where, $\lambda$: wavelength, R: distance between a pupil and an image point (retina), (u, v): coordinate value of the retina in a plane having an image point O on the retina as the original point and orthogonal to an optical axis, and (x, y): coordinate value of an optical system in a pupil plane.

Besides, by multiplying the amplitude distribution U (u, v) of the point image by its complex conjugate, an intensity distribution (PSF)I(u, v) of the point image is obtained.

$$I(u, v)=U(u, v)U^*(u, v).$$

Further, the intensity distribution I (U, v) of the point image is subjected to Fourier transformation, and (R(r, s)) normalization of so-called spatial frequency conversion is performed, so that an OTF (Optical Transfer Function) is obtained.

$$R(r,s) = \int\int_{-\infty}^{\infty} I(u, v)e^{-i2\pi(ru+sv)'} dudv \quad (13)$$

Where, r, s: variable of spatial frequency region.

$$OTF(u, v)=R(r, s)/|R(0, 0)|$$

Besides, since the magnitude of the OTF is MTF, $$MTF(r, s)=|OTF(u, v)|$$

Next, based on the monochromatic MTF obtained as stated above, the white light MTF is calculated.

In order to obtain the white light MTF, first, the MTFs at the respective wavelengths are weighted and are added. Here, since the values of the MTFs are different from each other for the respective wavelengths, when the MTF at the wavelength $\lambda$ is expressed by $MTF_\lambda$, $$MTF(r, s) = \frac{\int \omega_\lambda MTF_\lambda(r, s)d\lambda}{\int \omega_\lambda d\lambda} \quad (14)$$

Here, visible light is greatly weighted and a calculation is made.

Specifically, when red, green and blue of the three primary colors (RGB) are, for example, 656.27 nm: 1, 587.56 nm; 2, and 486.13 nm: 1, $$MTF(r, s)=(1\times MTF_{656.27}+2\times MTF_{587.56}+1\times MTF_{487.13})/(1+2+1).$$

Besides, since the white light MTF is measured at only one wavelength (840 nm), it may be obtained by making a correction with respect to other wavelengths based on the measured results and correcting them to white. Specifically, the MTFs at the respective wavelengths are obtained in such a manner that in the case of the ocular aberration, when the measurement wavelength in the ophthalmic characteristic measuring apparatus is, for example, 840 nm, a color aberration $W_A(X, Y)$ corresponding to a deviation amount from a higher order aberration $W_{840}(x, y)$ at a wavelength of 840 nm is measured from a model eye, $W_{840}(x, y)$ is added to this color aberration $W_A(x, y)$, and the MTF is calculated from this higher order aberration. That is, $$W_\lambda(x, y)=W_{840}(x, y)+W_A(x, y).$$

Further, in the case of the corneal higher order aberration, although the measured corneal shape does not depend on the wavelength, the refractive index of the cornea used when the shape is converted into the higher order aberration depends on the wavelength, and the wavelength is one of parameters in the expression of the pupil function, and therefore, the MTF depends on the wavelength in this case as well.

(Concerning Strehl Ratio Included in Ocular Aberration Display Section and Corneal Aberration Display Section Displayed on the Display Section 230)

The Strehl ratio (here, S) is obtained by dividing the center intensity I(0, 0) of PSF as the intensity distribution of the point image obtained as described above by the center intensity $I_0$(0, 0) of PSF obtained in the case of an aplanatic optical system. That is, $$S=I(0, 0)/I_0(0, 0).$$

(Concerning Display and Appearance of Landolt's Ring Displayed on the Display Section 230, for Example, a Mark for Visual Acuity Test)

Figure 4:
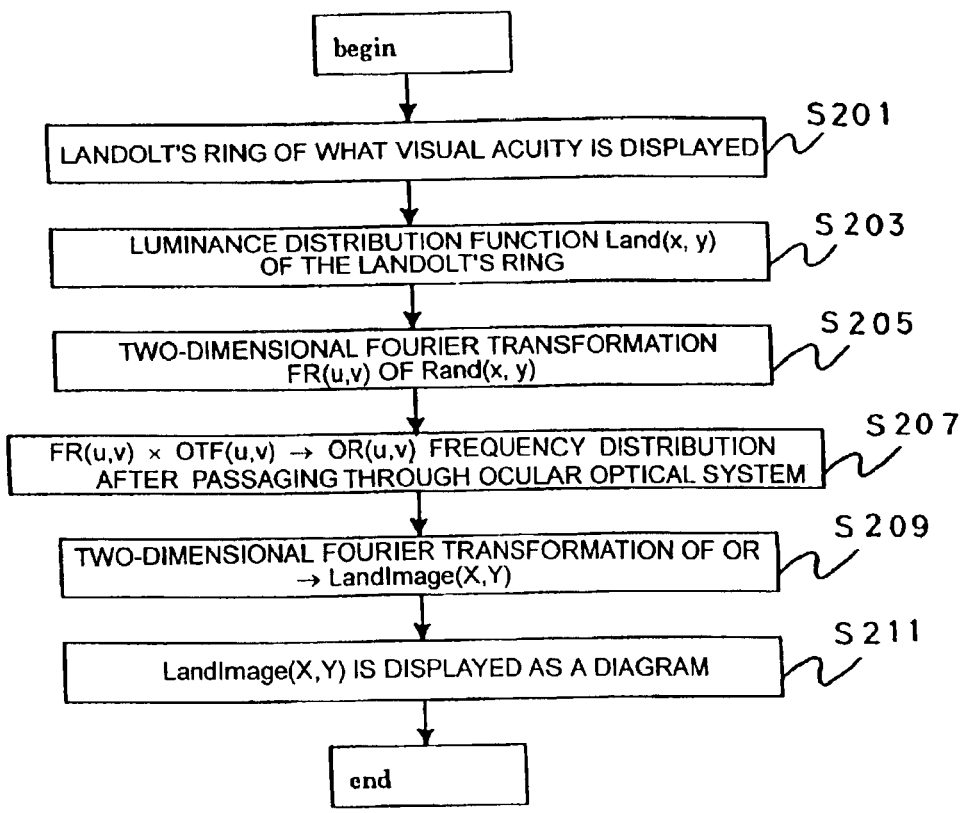
FIG. 4 is a flowchart relating to the display of a Landolt's ring.

FIG. 4 is a flowchart relating to the display of the Landolt's ring.

First, a measurer (for example, an eye doctor etc.) selects a specific one from Landolt's rings having sizes corresponding to suitable visual acuity for inspecting the visual acuity of a patient (S201). A luminance distribution function Land (x, y) indicating a pattern of this selected Landolt's ring is obtained or is previously stored, and this may be read out (S203). Here, the luminance distribution function Land(x, y) is obtained based on a deviation (value obtained by vector resolution of the length of the arrow given on the foregoing photographed raw image in the X direction and the Y direction) of the X-Y coordinate between the Hartmann plate 22 and the first light receiving section 23.

Next, two-dimensional Fourier transformation is performed for this luminance distribution function Land(x, y) to obtain FR(u, v) (S205). This FR(u,v) and the foregoing OTF (u, v) already obtained are convoluted to obtain OR(u, v) of a frequency distribution after passaging through the ocular optical system (S207). The two-dimensional inverse Fourier transformation is performed for this OR(u, v) to obtain the Land Image (X, Y) (S209).

The Land Image (X, Y) obtained at this step S209 is graphically displayed on the display screen of the display section 230 (S211). Incidentally, here, a display is such that the size of the pupil is $\phi 3$ (bright field) and is $\phi 7$ (dark field), and "visual acuity 0.7 Landolt's ring appearance" is displayed in both.

Hereinafter, a description will be given of first to thirteenth display examples in which the foregoing elements are collectively or selectively displayed. However, the same elements displayed on the display section 230 are designated by the same reference signs and their duplicate description will be omitted.

FIRST DISPLAY EXAMPLE

Figure 5:
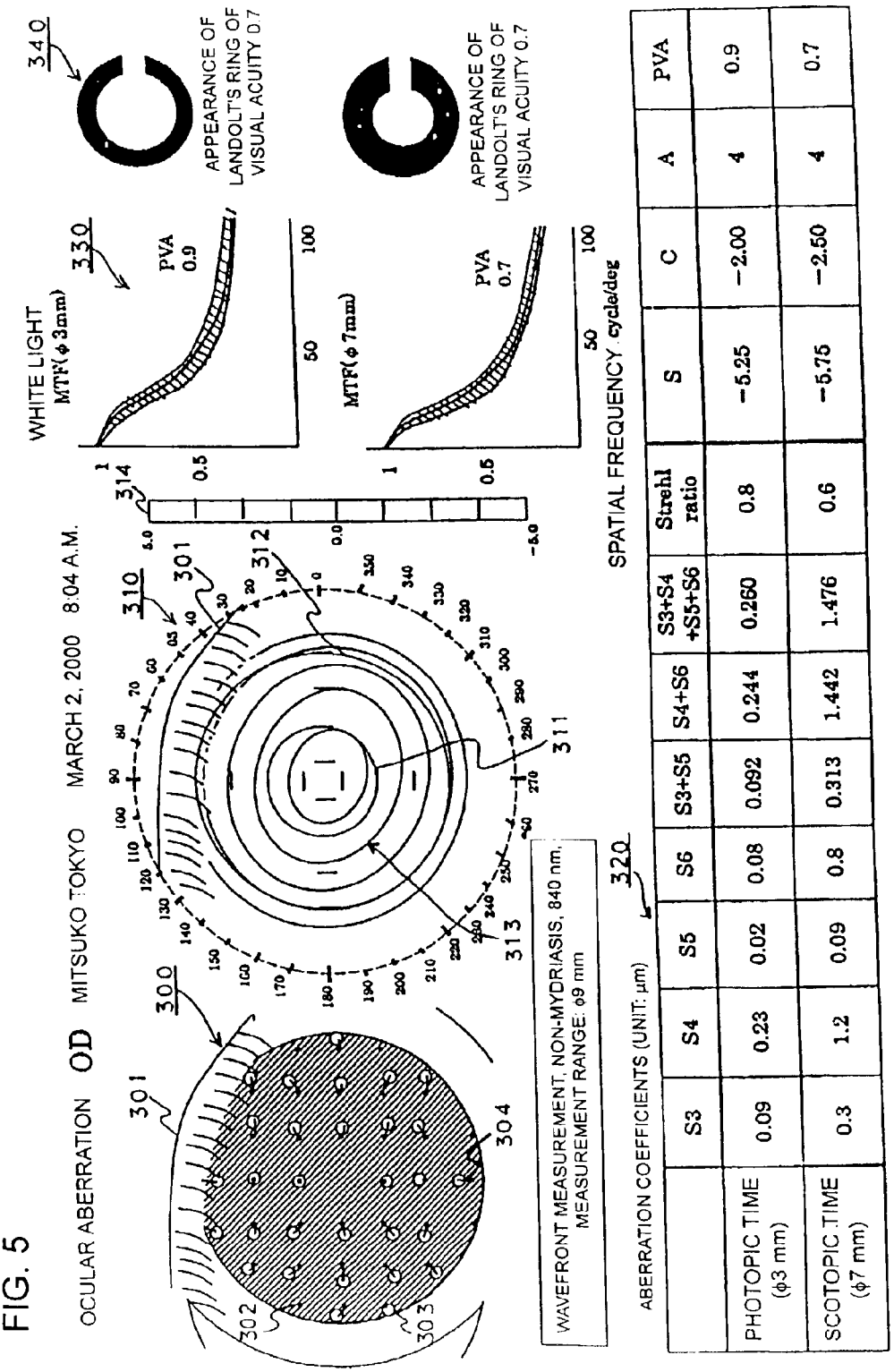
FIG. 5 is an explanatory view showing a first display example graphically displayed on a display section 230.

FIG. 5 is an explanatory view showing a first display example graphically displayed on the display section 230.

For example, a Hartmann image 300 as a photographed raw image, an ocular aberration map 310, an ocular aberration display section 320, a white light MTF display 330, and a Landolt's ring appearance display 340 are displayed on the display section 230. Incidentally, for example, a name of a patient (here, Mitsuko Tokyo), a measurement time (here, Mar. 2, 2000, 8:04 a.m.), plural measurement conditions (here, wavefront measurement as the kind of measurement, non-mydriasis as the kind of the eye 60 to be measured, 840 nm as the measurement wavelength, and $\phi 9$ mm as the measurement range of the eye 60 to be measured) are displayed on the display section 230.

The Hartmann image 300 is an image based on, for example, the reflected light from the retina 61 of the patient's eye 60 to be measured, and here, an eyelid 301 of the patient is also displayed. Besides, the Hartmann image 300 includes image points 302 in the case where plural substantially parallel light fluxes are assumed to be received on the first light receiving section 23 through the Hartmann plate 22, and region points 303 in the case where the reflected light from the retina 61 of the eye 60 to be measured is received on the first light receiving section 23 as light fluxes substantially expanding outside through the transmission parts or opening parts bored in the Hartmann plate 22. Besides, values obtained by subjecting a solid line 304 (its start point is the image point 302 and its end point is the center of gravity of the region point 303) displayed on the Hartmann image 300 to vector resolution along vertical and horizontal coordinate axes of the first light receiving section 23 are those obtained by converting the variation of the light flux into numbers, and correspond to $\Delta x$ and $\Delta y$ required when the foregoing Zernike coefficients are obtained. Incidentally, the solid line 304 as a difference between the image point 302 and the region point 304 corresponds to the higher order aberration of the eye 60 to be measured.

The ocular aberration map 310 includes, for example, a co-axial circle 311 indicating the pupil (here, $\phi 3$ mm) in the bright field, a co-axial circle 312 indicating the pupil (here, $\phi 7$ mm) in the dark field, and plural substantially elliptic rings 313 expressing the higher order aberrations, which are calculated from the Zernike coefficients in consideration of the deviation of the light flux, by contour lines. Incidentally, the outer peripheral edge of the ocular aberration map 310 has graduations for every 10° (0 to 360), and is visually easy to see. Besides, a scale (for example, graduations of −5.0 to 5.0 for every 1.0 $\mu$m) 314 corresponding to the measurement range of the eye 60 to be measured is indicated in the vicinity of the ocular aberration map 310.

Here, as the higher order aberrations, all aberrations including a low order aberration of the eye to be measured or high order (third-order or higher) aberrations are displayed as the need arises. The higher order aberrations are graphically displayed by changing color, density or the like as the need arises. Besides, in all aberrations, although second-order and higher aberrations are displayed as initial values, it is also possible to make such a selection that the primary and higher aberrations are displayed as all aberrations.

Various numerical data in the bright field (here, $\phi 3$ mm) and the dark field (here, $\phi 7$ mm) are displayed in the ocular aberration display section 320. Specifically, they are aberration components (for example, coma aberration, spherical aberration) of the eye 60 to be measured calculated by using the foregoing Zernike coefficients, and aberration coefficients S3, S4, S5, S6, S3+S5, S4+S6, S3+S4+S5+S6 as numerical data, numerical data of the so-called Strehl ratio used as an index of viewability, refractive power (here, it is indicated by S and has unit D: so-called diopter value) as 1/(ocular focal distance), astigmatic degree (here, it is indicated by C and has unit D), an astigmatic axis (here, it is indicated by A and has unit °), and visual acuity (here, PVA) are respectively displayed. Here, the refractive power and the astigmatic degree are obtained from the secondary term (S2) of the Zernike coefficients. Incidentally, the plural substantially elliptic rings 313 displayed on the ocular aberration map 310 are obtained in consideration of these aberration coefficients.

As described above, the white light MTF display 330 is an index indicating the appearance of sine wave lattices and the like, and here, it is indicated as a graph in which the horizontal axis is a spatial frequency (cycle/deg) (value corresponding to, for example, a case where 0 to 100 black lines per 1° are given), and the vertical axis is a degree (0 to 1) of appearance of a white and black pattern. Specifically, here, a graph in a case of the bright field (here, $\phi 3$ mm) and visual acuity of 0.9 and a graph in a case of the dark field (here, $\phi 7$ mm) and visual acuity of 0.7 are collectively displayed so that they can be compared with each other. Incidentally, oblique lines on the graphs indicate a normal range.

The Landolt's ring appearance display 340 indicates how a mark for visual acuity inspection is seen on the retina 61 of the patient. The Landolt's ring appearance display 340 indicates that for example, in the case of the bright field (here, $\phi 3$ mm) and the measured results, the Landolt's ring corresponding to the visual acuity of 0.7 does not blur and is seen to be slender and fine, and in the case of the dark field (here, $\phi 7$ mm) and the measured results, it slightly blurs and is seen to be thick.

Figure 6:
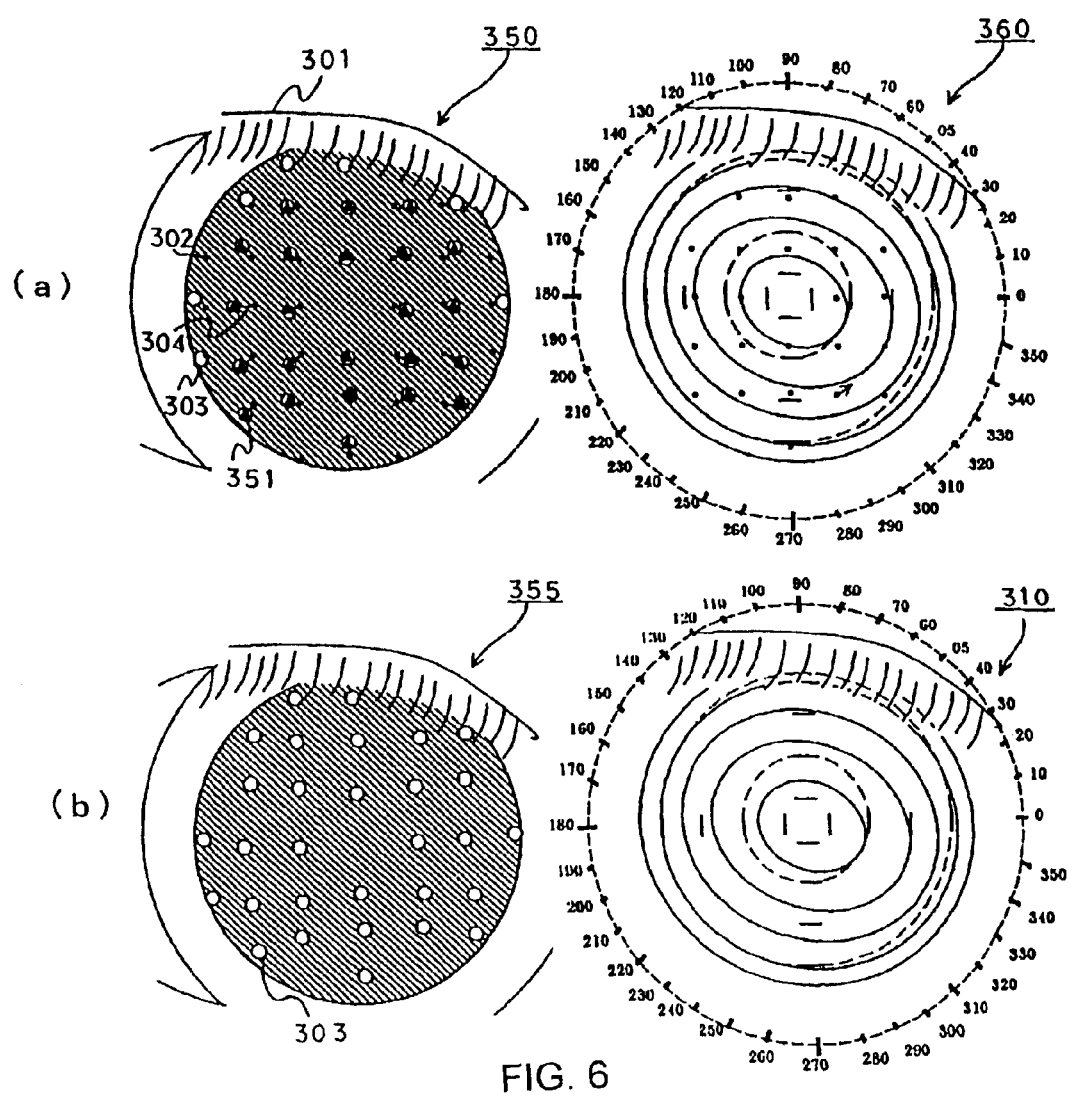
FIG. 6 is an explanatory view (1), (2) showing a modified example of the first display example.

FIG. 6(a) is an explanatory view (1) showing a modified example of the first display example.

Here, in comparison with the display section 230 of the first display example, an example is given which displays a Hartmann image 350 in which the center of gravity of an image point used for measurement of the higher order aberration is indicated as a blackened triangle 351 in the Hartmann image 300 as the photographed raw image. In the drawing of the Hartmann image 350, and in the blackened triangle 351, a lattice point (small hole, opening or transmission portion) provided in the Hartmann plate and a measured irradiation region point are made to correspond with each other, and it is disposed at the center-of-gravity position of the irradiation region. The center-of-gravity position is obtained by a method such as a so-called moment method based on irradiation intensity and irradiation position.

Besides, here, in comparison with the display section 230 of the first display example, an example is given in which in addition to the ocular aberration map 310, an ocular aberration map 360 is displayed in which lattice points having correspondence and provided on the Hartmann plate with measured results are overlay-displayed.

FIG. 6(b) is an explanatory view (2) showing a modified example of the first display example.

Here, in comparison with the display section 230 of the first display example, an example is given in which the Hartmann image 300, which is the photographed raw image, itself 355 is displayed.

Figure 7:
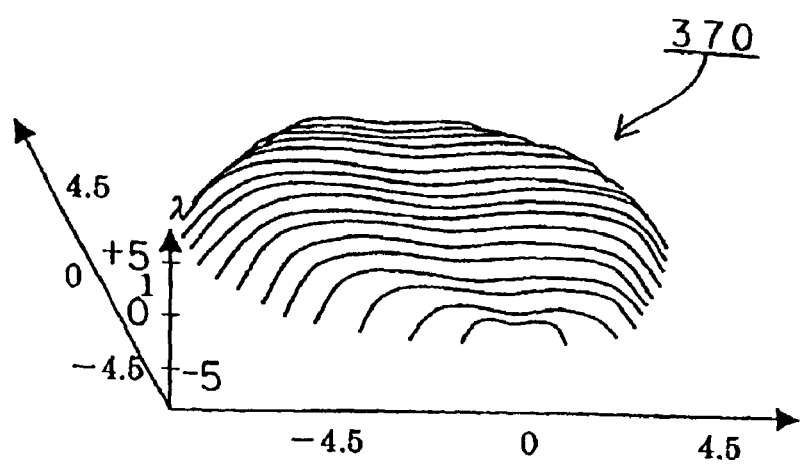
FIG. 7 is an explanatory view (3) showing a modified example of the first display example.

FIG. 7 is an explanatory view (3) showing a modified example of the first display example.

Here, in comparison with the display section 230 of the first display example, an example is given in which instead of the ocular aberration map 310, a bird's eye map 370 indicating a three-dimensional shape in the measurement range of the eye 60 to be measured is displayed. The bird's eye map 370 displays the three-dimensional shape using a plane scale (here, −4.5 to 4.5) with the center point of the pupil as the origin in accordance with the measurement range +9 mm, and a solid scale (here, −5.0 to +5.0 μm). Incidentally, in the display section 2309, a suitable display pattern can be selected and prepared by using the foregoing Hartmann images 300 and 350, the ocular aberration maps 310 and 360, and the bird's eye map 370.

Besides, according to the foregoing display examples, the aberration coefficients at the photopic time (pupil diameter is small, for example, φ3 mm) and the scotopic time (pupil diameter is large, for example, φ7 mm) are displayed, so that both can be compared with each other. Besides, numerical data which can be precious data based on which for example, an eye doctor, an inspector or the like judges that the value of the displayed aberration coefficient is large and some measure (for example, medical treatment by going to hospital or entering hospital) is necessary, can be displayed according to the degree of caution, for example, the color is changed like blue→light blue→yellow green→yellow→red as a distance from a normal value becomes large.

Besides, also with respect to the white light MTF display 330, a display in both the bright field and dark field can be performed. Besides, a display of corrected vision may be performed from the coefficients obtained by the measurement. Further, based on the corrected vision, a presumed appearance of Landolt's ring may be displayed. Besides, as the unit of the aberration, any of μm, nm and λ may be selected. Besides, a display of both eyes may be selected.

SECOND DISPLAY EXAMPLE

Figure 8:
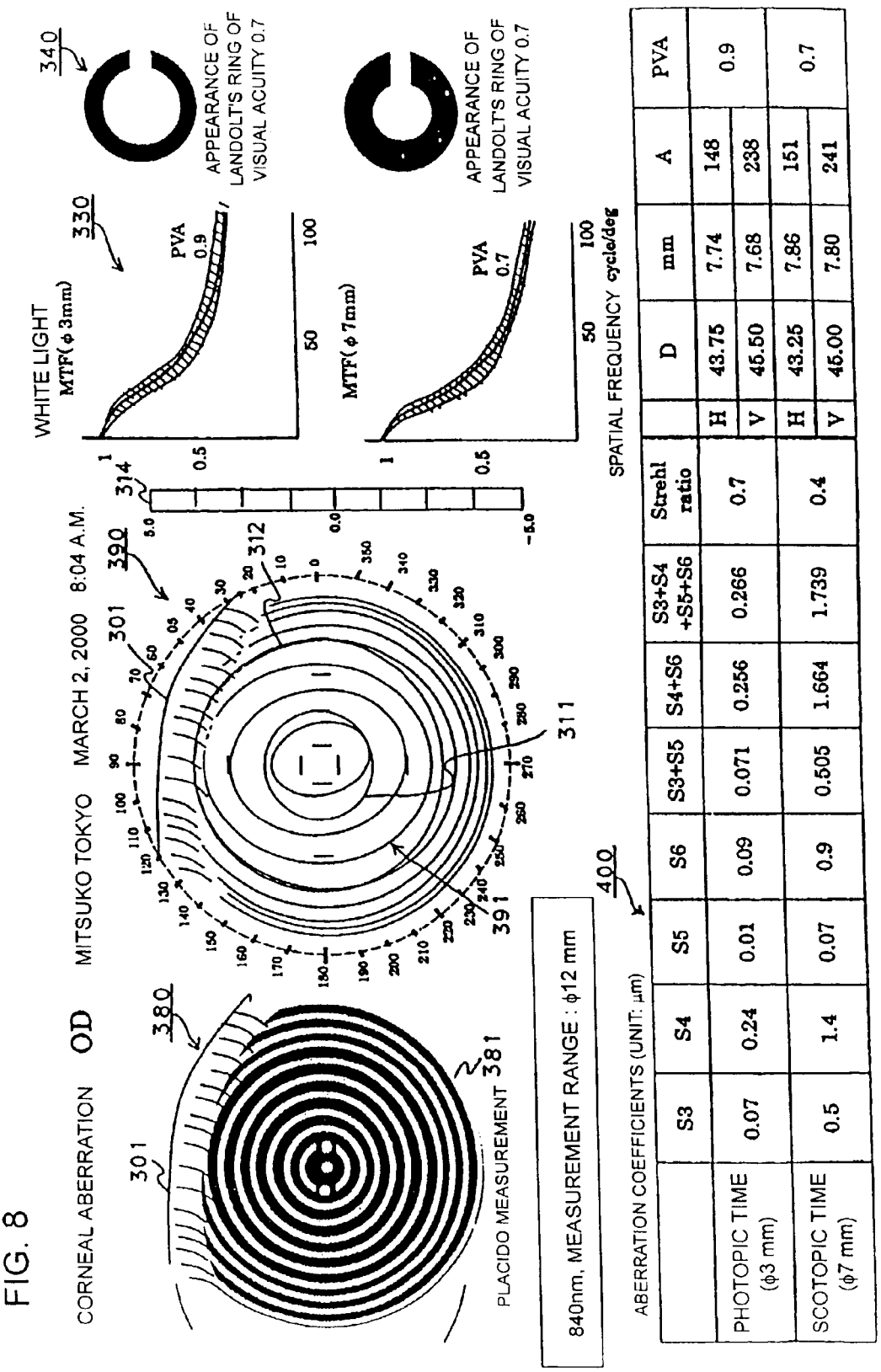
FIG. 8 is an explanatory view showing a second display example graphically displayed on the display section 230.

FIG. 8 is an explanatory view showing a second display example graphically displayed on the display section 230.

For example, a display 380 of placido measurement, a corneal aberration map 390, a corneal aberration display section 400, a display 330 of white light MTF (φ3, φ7 mm) and a Landolt's ring appearance display 340 are displayed on the display section 230. Incidentally, the measurement range of the eye 60 to be measured here is, for example, φ12 mm.

As described above, the display 380 of the placido measurement is a display based on received optical signals obtained in such a manner that after alignment adjustment is completed, the light flux from the third light source section 51 is irradiated onto the cornea 62 of the eye 60 to be measured using the placido ring 41 for projecting the index of a pattern made of the plural co-axial rings 381, and the reflected light from the cornea 62 with the plural co-axial rings 381 is received on the second light receiving section 35. Besides, it is also possible to make a measurement at the light receiving section 23 by removing or adjusting the Hartmann plate 22. Deviations from the co-axial circles in the respective coordinates of the measured placido ring 41 are made Δx and Δy, and similarly to the above, the Zernike coefficients are calculated, and the wavefront is further calculated, so that the corneal aberration can be obtained.

The corneal aberration map 390 includes a co-axial circle 311 indicating the pupil (here, φ3 mm) in the bright field, a co-axial circle 312 showing the pupil (here, φ7 mm) in the dark field, and contour lines 391 indicating the corneal aberration calculated from the Zernike coefficients in consideration of the deviation of the light flux. Incidentally, the outer peripheral edge of the corneal aberration map 390 has graduations (0 to 360) for every 10°, and is visually easy to see. Besides, a scale (for example, graduations of −5.0 to 5.0 for every 1.0 μm) 314 corresponding to the measurement range (here, φ12 mm) of the eye 60 to be measured is displayed in the vicinity of the corneal aberration map 390.

In comparison with the foregoing ocular aberration map 310, the corneal aberration display section 400 indicates a refractive power S as 1/(ocular focal distance (unit of meter)), an astigmatic degree C, a corneal aberration (here, indicated by D, unit D) as a degree when only the cornea is made an optical system instead of the astigmatic axis A, a radius of curvature in mm, axial direction (here, indicated by A, unit °), H indicating a place where the radius of curvature becomes maximum, and V indicating a place where the radius of curvature becomes minimum. Incidentally, while the ocular aberration display section 230 is calculated based on the whole eye (that is, the retina 61), the corneal aberration display section 400 is calculated based on only the cornea 62, and accordingly, the concrete numerical data indicated in the ocular aberration display section 320 and the corneal aberration display section 400 are different as shown in the drawings.

THIRD DISPLAY EXAMPLE

Figure 9:
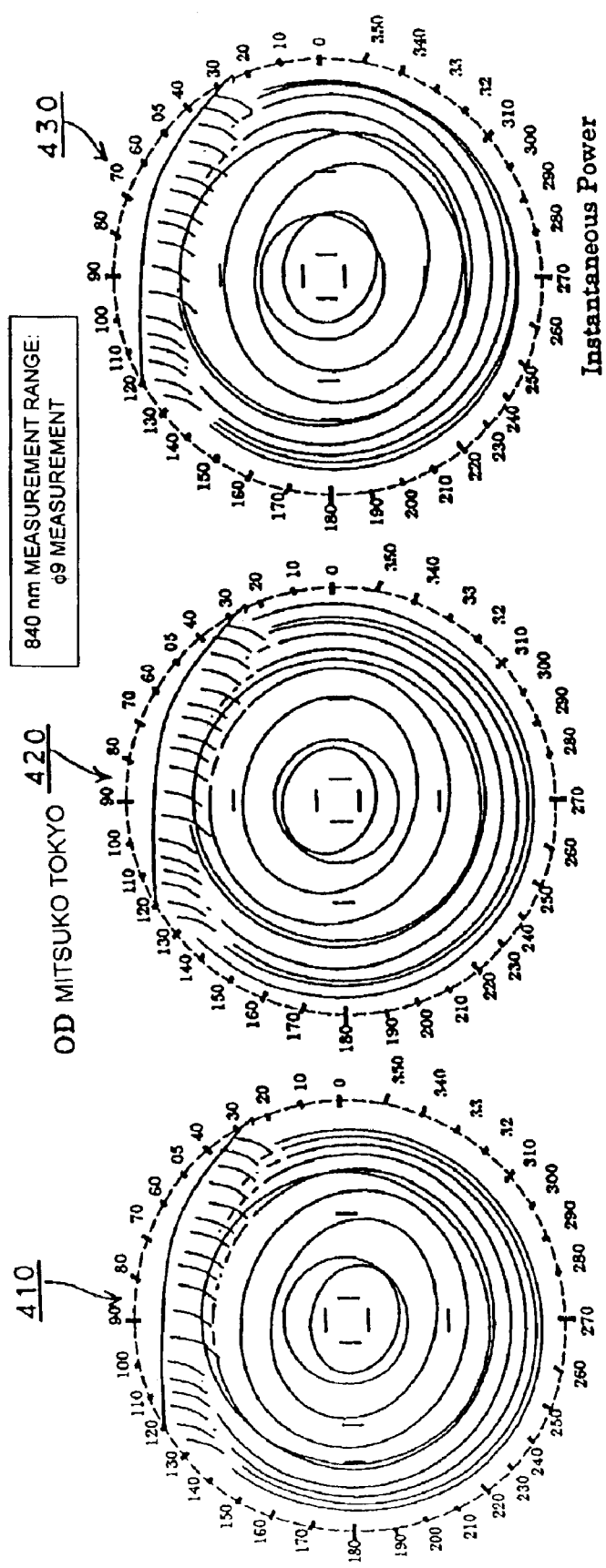
FIG. 9 is an explanatory view showing a third display example graphically displayed on the display section 230.

FIG. 9 is an explanatory view showing a third display example graphically displayed on the display section 230.

Here, in comparison with the display section 230 of the second display example, instead of the display 380 of placido measurement, an Axial Power map 410, a Refractive Power map 420, and an Instantaneous Power map 430 according to a cornea shape are collectively or selectively displayed. However, the measurement range here is, for example, φ9 mm, and the measurement range of the corneal aberration map 390 is also made to equivalent to this and a display is performed.

Besides, a scale (for example, graduations of 35.5 to 52.0 (D) for every 0.5D) corresponding to the measurement range (here, φ9 mm) of the eye 60 to be measured may be displayed in the vicinity of the Power maps 410, 420 and 430 according to the corneal shape (described later).

FOURTH DISPLAY EXAMPLE

Figure 10:
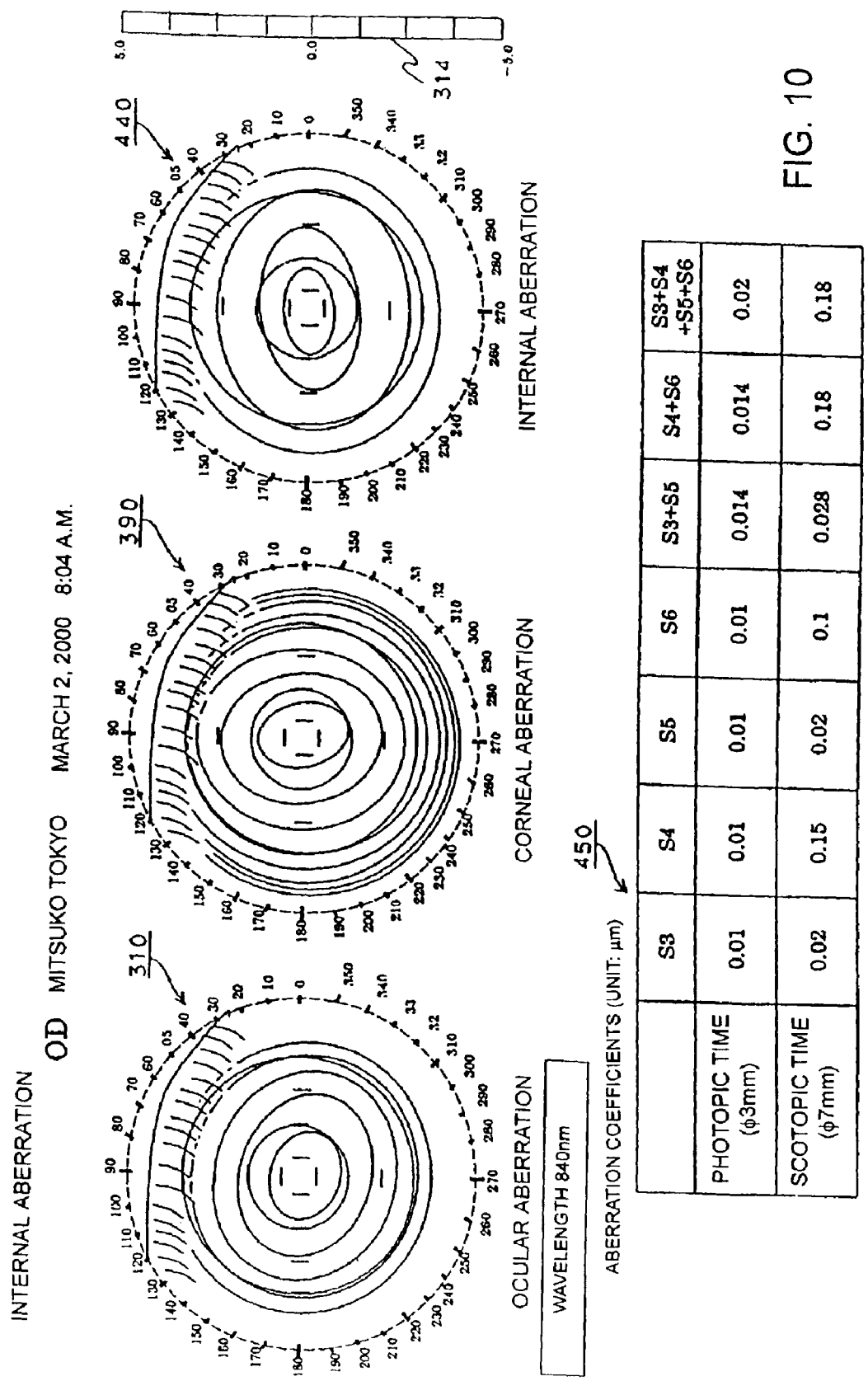
FIG. 10 is an explanatory view showing a fourth display example graphically displayed on the display section 230.

FIG. 10 is an explanatory view showing a fourth display example graphically displayed on the display section 230.

For example, an ocular aberration map 310, a corneal aberration map 390, an internal (inside) aberration map 440 calculated based on the ocular and the corneal aberration maps 310 and 390, and an aberration display section 450 are displayed on this display section 230. Besides, the internal (inside) aberration map 440 is displayed based on, for example, internal aberration coefficients displayed on the internal (inside) aberration map 440. The internal aberration coefficients are numerical data calculated by subtracting the corneal aberration coefficients for displaying the corneal aberration map 390 from the aberration coefficients of the whole eye for displaying the ocular aberration map 310.

According to this display example, the internal (inside) aberration is displayed, so that an influence, other than the corneal aberration, exerted on the ocular aberration can be considered.

Figure 11:
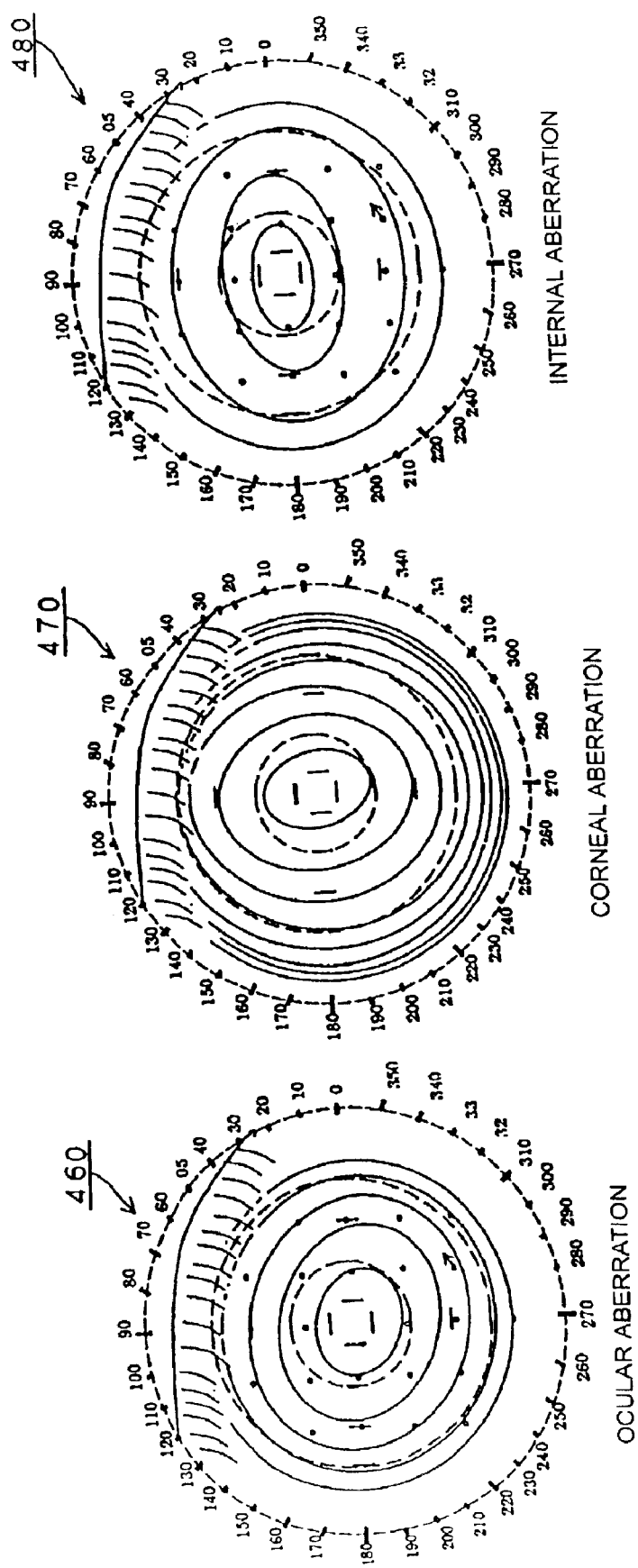
FIG. 11 is an explanatory view showing a modified example of the fourth display example.

FIG. 11 is an explanatory view showing a modified example of the fourth display example.

Here, in comparison with the display section 230 of the fourth display example, an example is given in which in addition to the ocular aberration map 310, the corneal aberration map 390, and the internal (inside) aberration map 440, an ocular aberration map 460, a corneal aberration map 470, and an internal (inside) aberration map 480, in which lattice points having correspondence and provided on the Hartmann plate with measured results are overlay-displayed on the color maps of the respective aberrations.

Figure 12:
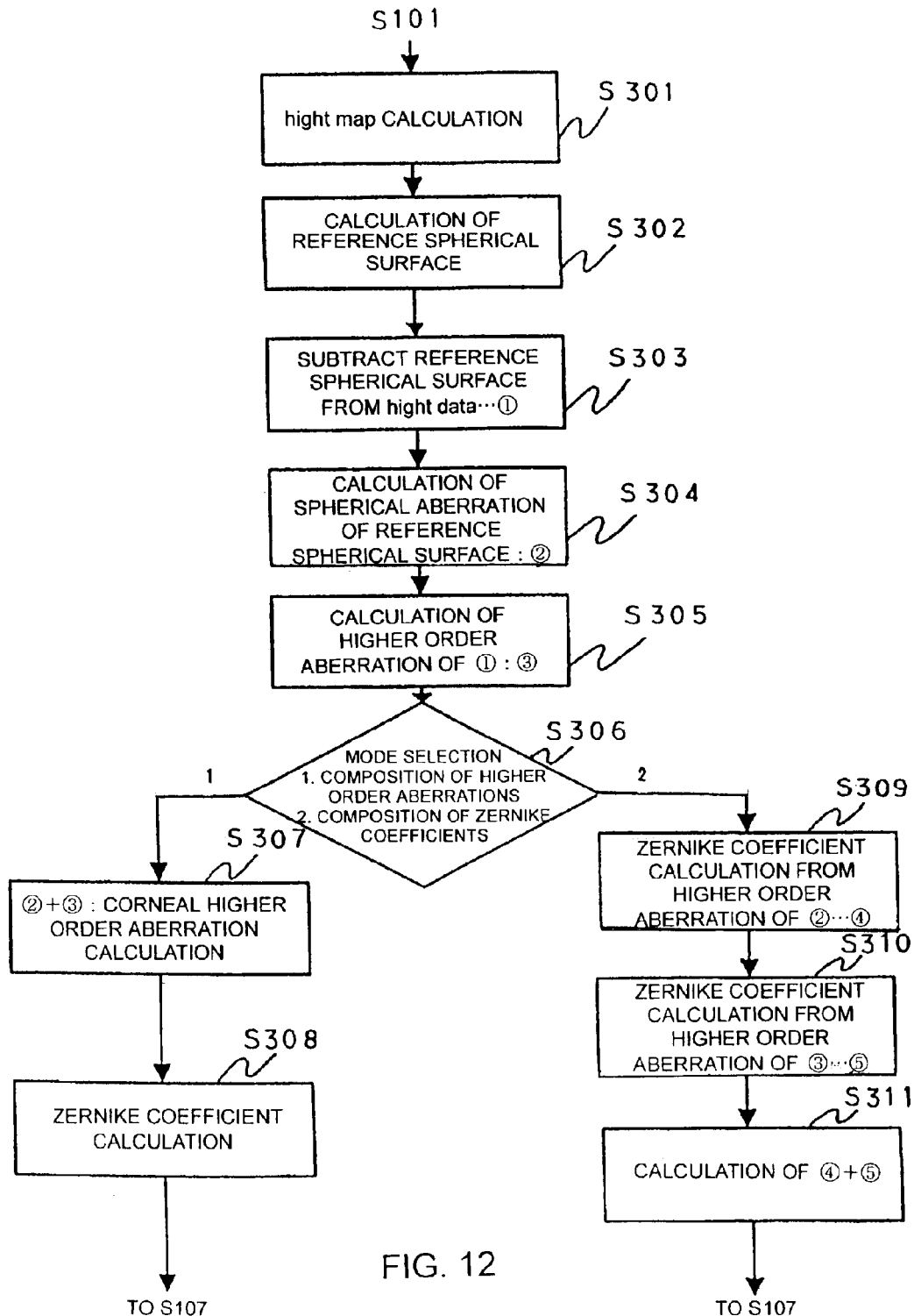
FIG. 12 is a flowchart showing corneal aberration measurement.

FIG. 12 is a flowchart showing corneal aberration measurement.

Here, especially, calculation (S103) of the Zernike coefficients in the case of corneal aberration measurement and wavefront calculation (S105) from the Zernike coefficients will be described in detail.

First, based on a signal from the second light receiving section 35, data of cornea shape map (High Map) which has a corneal vertex as a basis and indicates the height of the cornea shape in accordance with a light receiving position of the placido ring are calculated (S301). A shape of a reference spherical surface most fitted to the cornea shape obtained at the step S301 is calculated (S302). By this, the calculation accuracy of the Zernike coefficients can be improved. It is sufficient to obtain necessary places in accordance with the measurement range (for example, φ3, φ7).

Next, subtraction of a component of the reference spherical surface from a component of the cornea shape is performed (S303). By this, a residual component of only a difference from the reference spherical surface is obtained. Here, the spherical aberration of the reference spherical surface is calculated (S304). The higher order aberration of the residual component obtained at the step S303 is calculated (s305). Besides, a selection is made between a first mode in which the Zernike coefficients are calculated after the higher order aberrations of the measurement wavefront and the reference spherical surface are combined with each other, and a second measurement mode in which the Zernike coefficients are obtained for each of higher order aberrations of the measurement wavefront and the reference spherical surface and the Zernike coefficients are combined (S306).

Here, when the first measurement mode is selected, the procedure proceeds to step S307, and when the second measurement mode is selected, it proceeds to step S309.

In the first measurement mode, after the higher order aberration of the reference spherical surface obtained at the step S304 is added to the higher order aberration of the residual component obtained at the step S305, the higher order aberrations are obtained as the corneal higher order aberration (S307). Further, the Zernike coefficients of the corneal higher order aberration obtained at the step S307 are calculated (S308). Incidentally, the Zernike coefficients indicate the corneal aberration. When this is ended, the procedure proceeds to the step S107 of FIG. 3, a display mode is selected, and the procedure proceeds to the subsequent processing.

On the other hand, when the second measurement mode is selected at the step S306, the Zernike coefficients are calculated from the higher order aberration of the reference spherical surface (S309). Next, the Zernike coefficients are calculated from the higher order aberration of the residual component obtained at the step S305 (S310). The Zernike coefficients obtained at the steps S309 and S310 are combined to obtain the corneal aberration (S311). When this is ended, the procedure proceeds to the step S107 of FIG. 3, a display mode is selected, and the procedure proceeds to the subsequent processing.

FIFTH DISPLAY EXAMPLE

Figure 13:
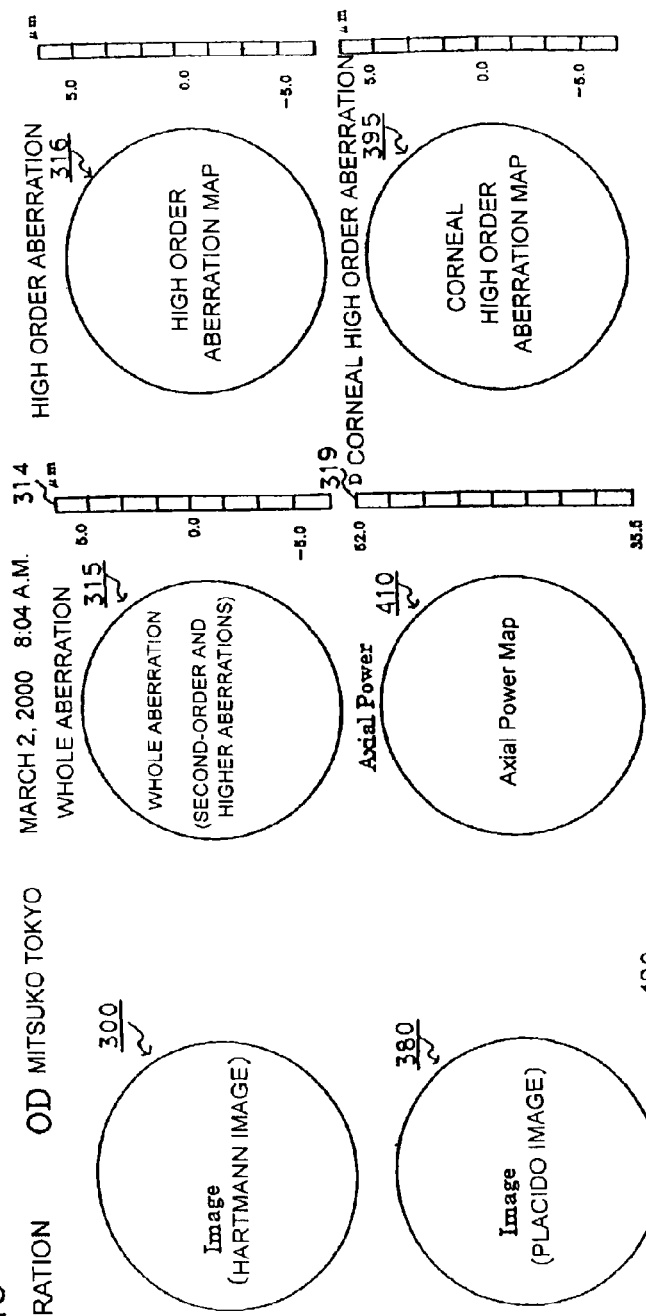
FIG. 13 is an explanatory view showing a fifth display example graphically displayed on the display section 230.

FIG. 13 is an explanatory view showing a fifth display example graphically displayed on the display section 230.

The display section 230 collectively displays, for example, ocular aberrations and corneal aberrations. The ocular aberration display includes a Hartmann image 300 (here, indicated by Image and the detailed image is omitted) as a photographed raw image shown in the first display example, a whole aberration 315 of the eye to be measured including at least second-order and higher aberrations, and a high order aberration 316 including third-order and higher aberrations. The corneal aberration display includes a placido image 380 (here, indicated by Image and its detailed image is omitted) as display of placido measurement shown in the second display example, an Axial Power map 410 shown in the third display example, and a cornea high order aberration map 395. Further, an ocular and corneal aberration display section 490 including numerical data corresponding to the ocular aberration and the corneal aberration is displayed on the display section 230.

Besides, the display mode of the whole aberration 315 and the high order aberration 316 is substantially similar to the ocular aberration map 310 described in detail in the first display example, and here, its detailed display is omitted. Besides, the display mode of the corneal high order aberration map 395 is substantially similar to the corneal aberration map 390 described in detail in the second display example, and here, its detailed display is omitted.

Besides, a scale 314 displayed in the vicinity of each of the maps is the same as the scale described in detail in the first display example. Incidentally, the scale unit of the scale 314 can be suitably changed, and for example, the scale unit of the whole aberration 315 may be set to not only −5.0 to 5.0 μm, but also −10.0 to 10.0 μm, or −15.0 to 15.0 μm. As stated above, by changing the scale unit, a change at a time when the spherical degree is high can also be displayed intelligibly.

Besides, a scale 319 indicating a diopter value (D) is displayed in the vicinity of the Axial Power map 410. Here, the scale 319 displayed in the vicinity of each of the maps is the same as the scale described in detail in the second display example. Incidentally, the scale unit of the scale 319 can be suitably changed and is not limited to 35.5 to 52.0 (D).

Besides, here, although the Axial Power map 410 is displayed as the corneal Power map, instead of the Axial Power map 410, for example, the Refractive Power 420 shown in the third display example, the Instantaneous Power 430, and all aberrations of second order or higher or primary or higher (selectable) in which a coefficient $C_{21}$ of a term equivalent to a spherical component of all aberrations of the after-mentioned cornea obtained from the Zernike coefficients is replaced by a coefficient $C_{21}$ of a term equivalent to a spherical component among Zernike coefficients expressing all the ocular aberrations, may be selectively displayed. Besides, the display region of each of the aberration maps may display an aberration map calculated with a pupil diameter (for example, φ6) at the scotopic time or with a pupil diameter (for example, φ8) of mydriasis may be displayed. Incidentally, the display region of the corneal Power map can be changed.

Besides, in the ocular and the corneal aberration display section 490, for example, the ocular aberration corresponds to the ocular aberration display section 320 shown in the first display example, and similarly, the corneal aberration display corresponds to the corneal display section 400 shown in the second display example. However, here, numerical data concerning the after-mentioned mydriasis is also displayed. The ocular and corneal aberration display section 490 displays numerical data divided into parts of the photopic time, the scotopic time, and the mydriasis according to the diameter of the pupil. Incidentally, here, since suitable numerical data are displayed, concrete numerical values are omitted.

Here, the photopic time is so-called photopic vision, and means a state in which observation is made at the brightness of relatively high level luminance $cd/m^2$ or higher, and physiologically, a state where an object is seen by only cones. The scotopic time is so-called scotopic, and is a state where observation is made at dark and low brightness level luminance (for example, $10^{-2}$ $cd/m^2$), and physiologically, a state where an object is seen by only rods. Besides, the mydriasis is so-called dilate, and means a state where a pupil diameter is further expanded as compared with that at general scotopic, and means a state in which for example, in the case where a test subject spends a long time in a place darker than the scotopic time, the pupil of the test subject naturally becomes larger than that at the scotopic time. Incidentally, the pupil diameters corresponding to the photopic time, the scotopic time and the mydriasis can be respectively changed. Besides, with respect to the display of the mydriasis, display/non-display can be selected.

Besides, here, although the whole aberration map 315 is made at least second-order and higher aberrations, when the primary aberration (tilt) is included, it is expected that a specific shape of, for example, a conical cornea or the like can be displayed, and therefore, the primary aberration or higher may be displayed as the whole aberration.

SIXTH DISPLAY EXAMPLE

Figure 14:
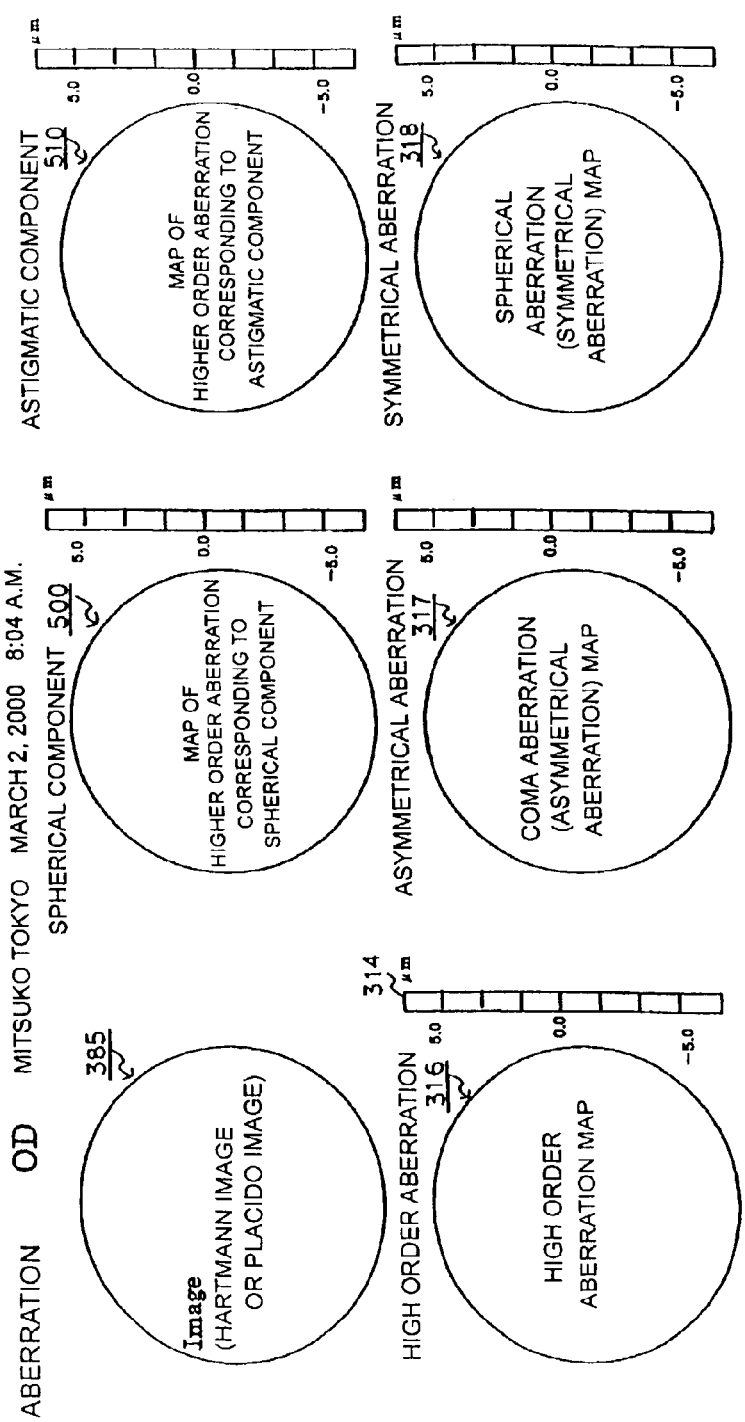
FIG. 14 is an explanatory view showing a sixth display example graphically displayed on the display section 230.

FIG. 14 is an explanatory view showing a sixth display example graphically displayed on the display section 230.

The display section 230 selectively displays, for example, ocular aberrations and corneal aberrations, and here, for convenience of explanation, two patterns of the ocular aberrations and the corneal aberrations are indicated. The ocular aberration display includes a Hartmann image 300 (here, indicated by Image 385, and its detailed image is omitted) as a photographed raw image shown in the first display example, a high order aberration 316 including third-order and higher aberrations, a coma aberration map 317 in which the respective high order aberrations included in the high order aberration 316 are divided into asymmetrical aberrations and symmetrical aberrations, a spherical aberration map 318, a map 500 of a higher order aberration S corresponding to a spherical component, and a map 510 of a higher order aberration C corresponding to astigmatism (astigmatic component).

Besides, since the corneal aberration is substantially equal to the ocular aberration display except that instead of the foregoing Hartmann image 300, a placido image 380 (here, indicated by Image 385, and its detailed image is omitted) as the display of the placido measurement shown in the second display example is displayed, the description will be omitted. Incidentally, in comparison with the ocular and corneal aberration display section 490 in which the ocular and corneal aberrations are collectively displayed and which is shown in the display example of FIG. 5, the ocular aberrations or the corneal aberrations are selectively displayed on the ocular and corneal aberration display section 495.

Here, the map 500 of the higher order aberration S corresponding to the spherical component is calculated based on, for example, a diopter value ($S_{motor}$) corresponding to a movement amount of the first light receiving optical system 20 by the second driving section 260, and a value obtained by converting Zernike coefficients corresponding to the spherical component obtained from the obtained Hartmann image 300 into a diopter value. That is, $$S = S_{motor} - 2C_{21}/(rc)^2.$$

Where, $S_{motor}$: diopter values corresponding to movement amounts of the first and the second driving sections 250 and 260, rc: pupil diameter to be analyzed and displayed on the map.

On the other hand, in the case where the map 500 of this higher order aberration S is displayed, calculation is made by converting the diopter value ($S_{motor}$) corresponding to the movement amount of the first light receiving optical system 20 into the Zernike coefficients, and adding the Zernike coefficients corresponding to the spherical component obtained from the Hartmann image 300 to this.

Figure 15:
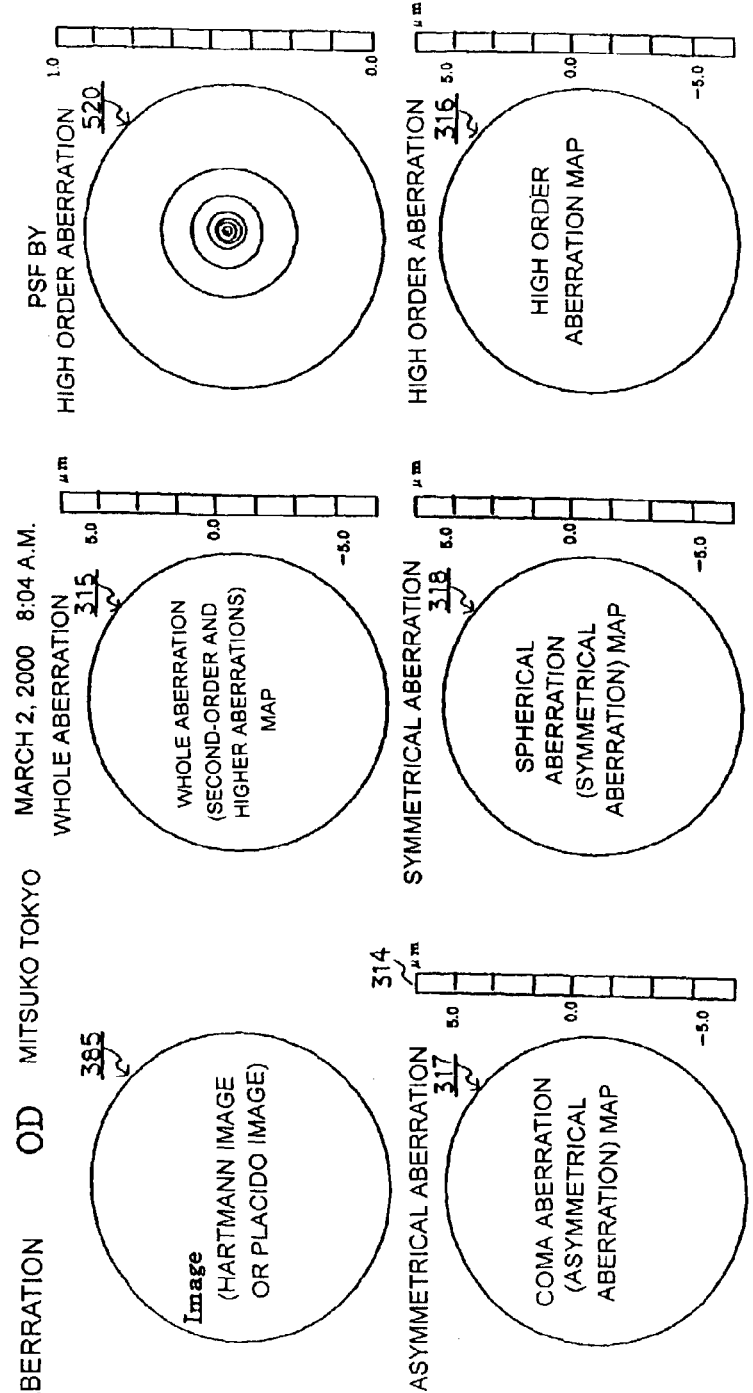
FIG. 15 is an explanatory view showing a modified example of the sixth display example.

FIG. 15 is an explanatory view showing a modified example of the sixth display example.

Here, in comparison with the display section 230 of the sixth display example, an example is given in which instead of the map 500 of the higher order aberration S corresponding to the spherical component, and the map 510 of the higher order aberration C corresponding to the astigmatism (astigmatic component), the whole aberration map 315 shown in the fifth display example, a point strength distribution (PSF) 520 calculated from the whole aberration map 315 and the high order aberration map 316 shown in the sixth display example is displayed, and the display positions of the high order aberration map 316, the coma aberration map 317, and the spherical aberration map 318 are changed and they are displayed.

Besides, in the display of the point strength distribution (PSF) 520, it is possible to select a mode in which the point strength distribution (PSF) receiving an influence of third-order and higher aberrations is displayed, and a mode in which the point strength distribution (PSF) of all the aberrations including the second order or higher is displayed.

Incidentally, the ocular and corneal aberration display section 495 is the same as that of the sixth display example, and its description will be omitted.

SEVENTH DISPLAY EXAMPLE

Figure 16:
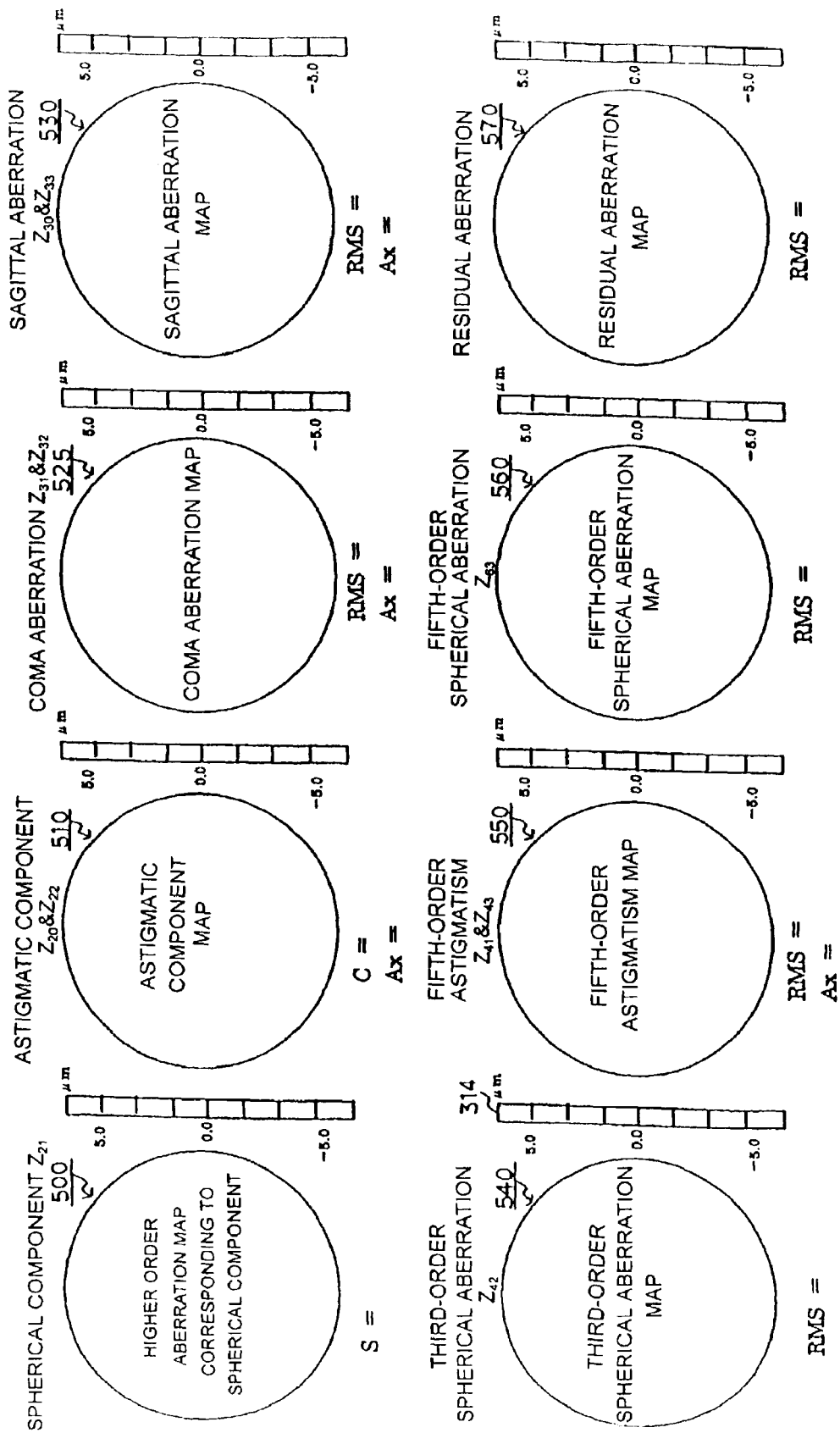
FIG. 16 is an explanatory view showing a seventh display example graphically displayed on the display section 230.

FIG. 16 is an explanatory view showing a seventh display example graphically displayed on the display section 230.

The display section 230 individually displays ocular aberrations and corneal aberrations, and with respect to the ocular and corneal aberrations, the respective aberrations are displayed as, for example, a spherical component, an astigmatic component, a coma aberration, a sagittal aberration, and a residual aberration. Specifically, a map 500 of a higher order aberration S corresponding to the spherical component shown in the sixth display example, a map 510 of a higher order aberration C corresponding to astigmatism (astigmatic component), a coma aberration map 525, a sagittal aberration map 530, a third-order spherical aberration map 540, a fifth-order astigmatism map 550, a fifth-order spherical aberration map 560, and a residual aberration map 570 are respectively displayed on the display section 230. Incidentally, the display mode of each of the higher order aberrations is the same mode as the ocular aberration map shown in the first display example, and its detailed display is omitted.

Here, returning to FIG. 18, the description will be continued. The map 510 of the higher order aberration C corresponds to the item 607 of the third-order astigmatism. The respective values set forth in the item 607 are displayed on the Zernike aberration coefficient (C=) and direction (Ax=) displayed in the vicinity of the higher order aberration map 510. The coma aberration map 525 corresponds to the item 604 of the third-order coma aberration. The respective values set forth in the item 604 are displayed on the mean square error (RMS=) of the aberration coefficients and direction (Ax=) displayed in the vicinity of this coma aberration map 525.

The sagittal aberration map 530 corresponds to the item 605 of the sagittal aberration. The respective values set forth in the item 605 are displayed on the mean square error (RMS=) of the aberration coefficients and direction (Ax=) displayed in the vicinity of this sagittal aberration map 530. The third-order spherical aberration map 540 corresponds to the item 601 of the third-order spherical aberration. The respective values set forth in the item 601 are displayed on the mean square error (RMS=) of the aberration coefficients displayed in the vicinity of the third spherical aberration map 540.

The fifth-order astigmatism map 550 corresponds to the item 608 of the fifth-order astigmatism. The respective values set forth in the item 608 are displayed on the mean square error (RMS=) of the aberration coefficients and direction (Ax=) displayed in the vicinity of this fifth-order astigmatism map 550. The fifth-order spherical aberration map 560 corresponds to the item 602 of the fifth-order spherical aberration. The value set forth in the item 602 is displayed on the mean square error (RMS=) of the aberration coefficients displayed in the vicinity of this fifth-order spherical aberration map 560.

The residual aberration map 570 means the total of the aberrations by terms (specifically, $Z_{40}$, $Z_{44}$, $Z_{50}$, $Z_{51}$, $Z_{52}$, $Z_{53}$, $Z_{54}$, $Z_{55}$, $Z_{60}$, $Z_{61}$, $Z_{62}$, $Z_{64}$, $Z_{65}$, $Z_{66}$, etc.) other then the respective terms of the Zernike polynomial used as the high order aberrations.

EIGHTH DISPLAY EXAMPLE

FIG. 17 is an explanatory view showing an eighth display example graphically displayed on the display section 230.

The display section 230 selectively displays ocular aberrations and corneal aberrations, and for example, a Hartmann image 300, a whole aberration map 315, an astigmatism+high order aberration map 580, and a high order aberration map 316 are displayed on the upper stage of the display section 230, and a spherical aberration (including the respective orders) 585, a coma aberration (including the respective orders) 590, a high order astigmatism (except for an astigmatic component) 595, and a sagittal aberration map 530 are displayed on the lower stage.

The astigmatism+high order aberration map 580 is displayed based on, for example, the high order aberration map 316 shown in the fifth display example and the higher order aberration map 510 corresponding to the astigmatic component shown in the sixth display example. The spherical aberration 585 is displayed based on, for example, the respective spherical aberrations of the foregoing orders. The coma aberration 590 is displayed based on, for example, the respective coma aberrations of the foregoing orders. The high order astigmatism 595 is displayed based on, for example, the respective high order astigmatisms of the foregoing orders (except for the third-order astigmatism corresponding to the astigmatic component).

NINTH DISPLAY EXAMPLE

Figure 22:
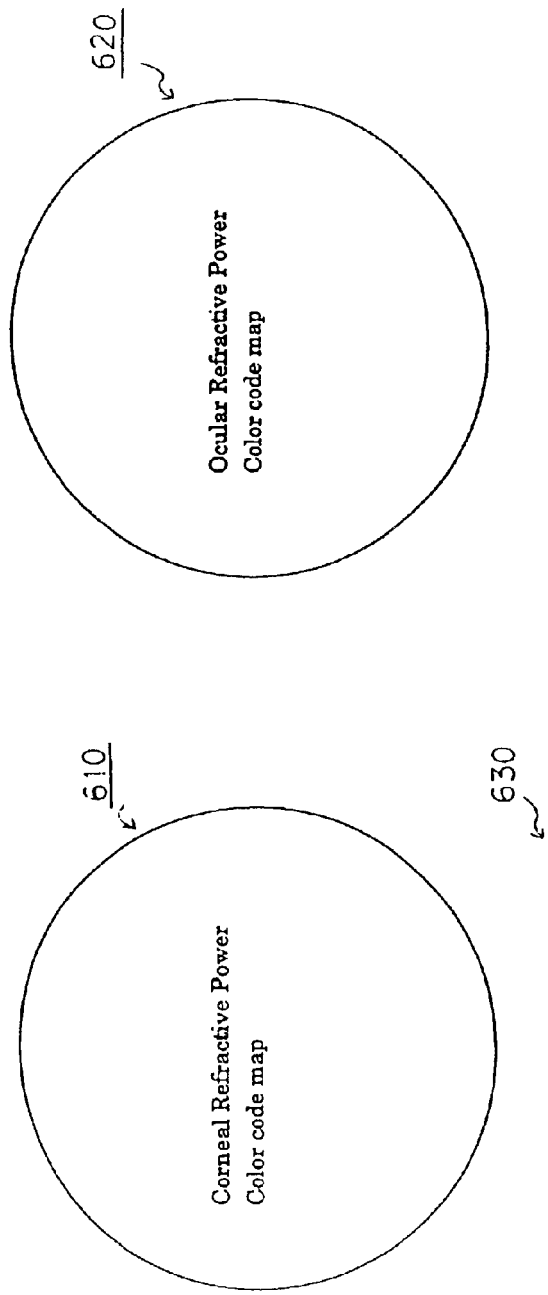
FIG. 22 is an explanatory view showing a ninth display example graphically displayed on the display section 230.

FIG. 22 is an explanatory view showing a ninth display example graphically displayed on the display section 230.

The display section 230 displays, for example, a corneal refractive power map 610, an ocular refractive power map 620, and a numerical data display section 630 relating to these displays. The display element of the numerical data display section 630 includes, for example, mean power concerning the photopic time and scotopic time, a spherical aberration, a coma aberration, an astigmatism, a sagittal aberration, a residual aberration and total. Incidentally, the display mode of the corneal refractive power 610 and the ocular refractive power map 620 is the same mode as the ocular aberration map described in detail in the first display example, and its detailed display example will be omitted. Incidentally, the unit is D (diopter). Besides, these displays may be made monochrome or color code maps as the need arises.

TENTH DISPLAY EXAMPLE

Figure 23:
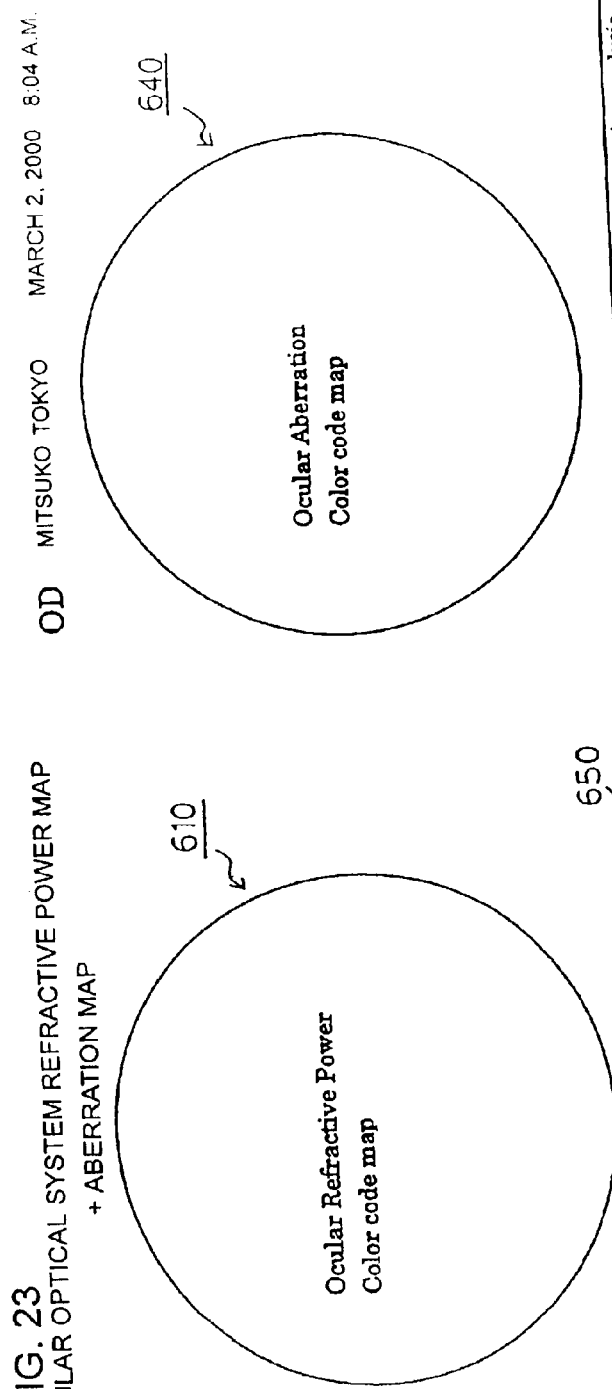
FIG. 23 is an explanatory view showing a tenth display example graphically displayed on the display section 230.

FIG. 23 is an explanatory view showing a tenth display example graphically displayed on the display section 230.

The display section 230 displays, for example, an ocular refractive power map 610, an ocular aberration map (high order aberration) 640, and a numerical data display section 650 relating to these displays. The display element of the numerical data display section 650 includes, for example, mean power concerning the photopic time and scotopic time, a spherical aberration, a coma aberration, an astigmatism, a sagittal aberration, a residual aberration, and total. Incidentally, the display modes of the ocular refractive power map 610 and the ocular aberration map (high order aberration) 640 are the same mode as the ocular aberration map shown in the first display example, and the detailed display example will be omitted. Besides, these displays may be made monochrome or color code maps as the need arises.

ELEVENTH DISPLAY EXAMPLE

FIG. 24 is an explanatory view showing an eleventh display example graphically displayed on the display section 230.

The display section 230 displays, for example, an ocular internal optics refractive power map 660 and a numerical data display section 670 concerning this display. The display element of this numerical data display section 670 includes, for example, mean power concerning the photopic time and scotopic time, a spherical aberration, a coma aberration, an astigmatism, a sagittal aberration, a residual aberration, and total. Incidentally, the display mode of the ocular internal optics refractive power map 660 is the same mode as the ocular aberration map shown in the first display example, and its display example will be omitted. Besides, the ocular internal optics refractive power map 660 can be obtained as, for example, a difference between the ocular refractive power map 620 shown in the ninth display example and the corneal refractive power map 610. Incidentally, the display here may be made a monochrome or color code map as the need arises.

TWELFTH DISPLAY EXAMPLE

Figure 25:
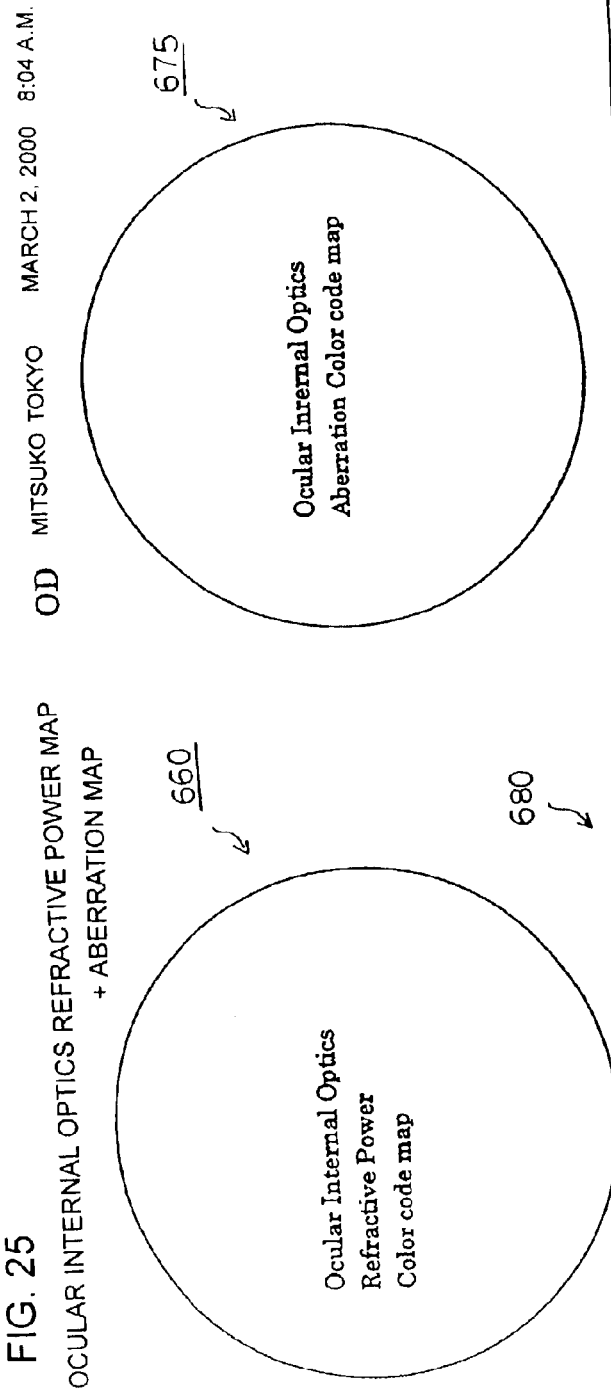
FIG. 25 is an explanatory view showing a twelfth display example graphically displayed on the display section 230.

FIG. 25 is an explanatory view showing a twelfth display example graphically displayed on the display section 230.

The display section 230 displays an ocular internal optics refractive power map 660, an ocular internal optics aberration map 675, and a numerical data display section 680 relating to the displays. The numerical data display section 680 includes various display elements as shown in the drawing. Besides, the display mode of the distribution here is the same mode as the ocular aberration map shown in the first display example, and its display example will be omitted.

Besides, the ocular internal optics refractive power map 660 is the same as the distribution shown in the eleventh display example. Besides, the ocular internal optics aberration map is the same as the internal aberrations 440 shown in the fourth display example. Incidentally, the display here may be made a monochrome or color code map as the need arises.

THIRTEENTH DISPLAY EXAMPLE

Figure 26:
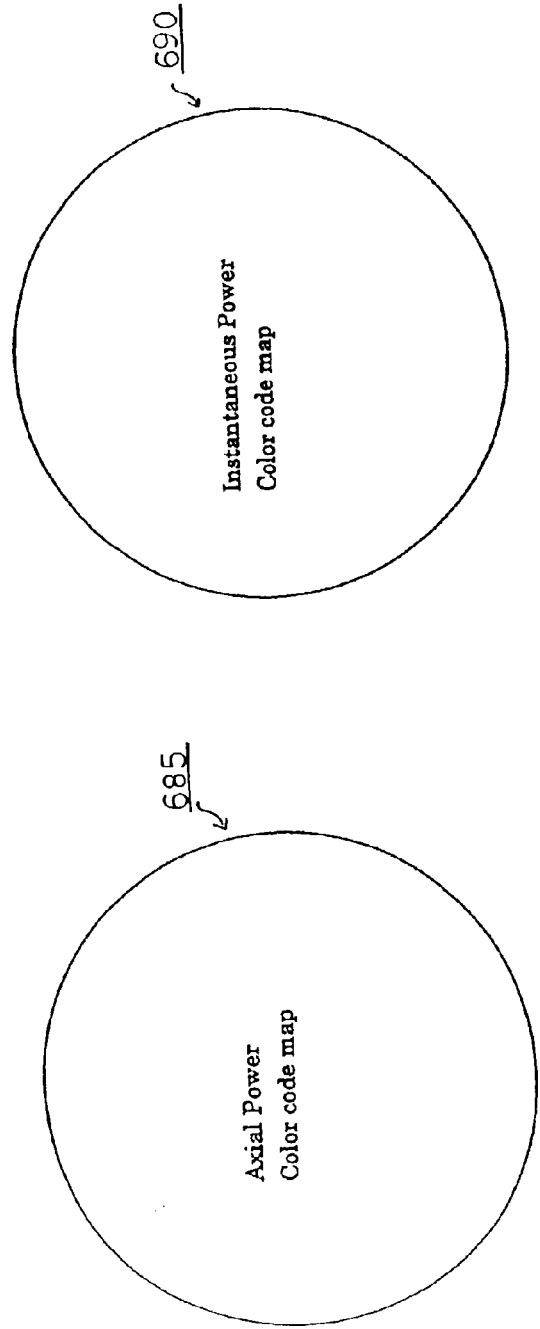
FIG. 26 is an explanatory view showing a thirteenth display example graphically displayed on the display section 230.

FIG. 26 is an explanatory view showing a thirteenth display example graphically displayed on the display section 230.

The display section 230 displays, for example, a corneal axial power map 685, an instantaneous power map 690, and a numerical data display section 695 relating to the display. The display element of this numerical data display section 695 includes, with respect to photopic time, scotopic time, and the whole cornea, for example, mean power, a spherical aberration, a coma aberration, an astigmatism, a sagittal aberration, a residual aberration, and total.

Besides, the display modes of the corneal axial power map 685 and the instantaneous power map 690 are the same mode as the ocular aberration map shown in the first display example, and its display example will be omitted. Besides, the display here may be made a monochrome or color code map as the need arises. Incidentally, values of φ for analysis of the photopic time, the scotopic time, and the whole cornea displayed on the numerical data display section can be suitably set.

As stated above, in the optical characteristic measuring apparatus 100 of this embodiment, for example, the measurement data (measured results) obtained under plural conditions, image data and/or numerical data corresponding to the measured results can be graphically displayed on the display section 230 collectively or selectively as the need arises. Incidentally, in all the Hartmann images and aberration drawings shown in the respective display examples, an anterior eye image, a spot center-of-gravity position capable of being used for analysis, and a reference lattice point corresponding to the spot center-of-gravity position can be respectively overlapped and displayed.

FOURTEENTH DISPLAY EXAMPLE

Figure 27:
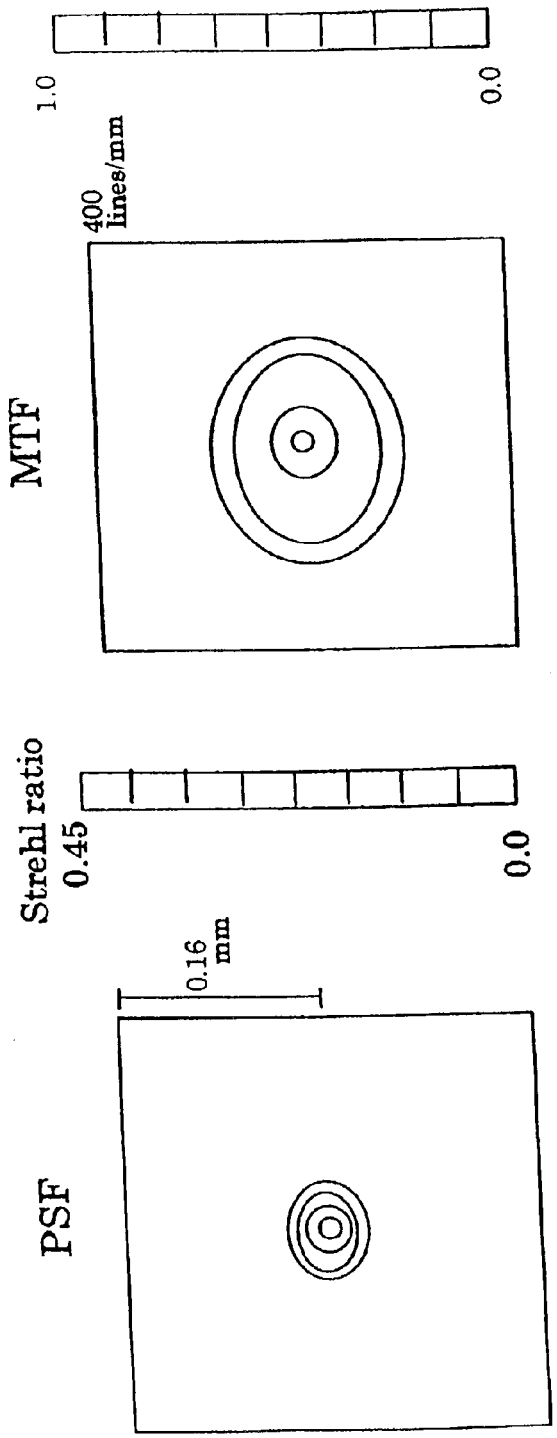
FIG. 27 is an explanatory view showing a fourteenth display example graphically displayed on the display section 230.

FIG. 27 is an explanatory view showing a fourteenth display example graphically displayed on the display section 230.

A display mode will be described which can be displayed instead of the MTF display shown in FIG. 5 as the first display example or shown in FIG. 8 as the second display example, or in addition to this.

A drawing in which PSF indicating the optical characteristics of the eye 60 to be measured is shown on a plane by contour lines is arranged at the left side of FIG. 27, and a drawing in which MTF is shown on a plane by contour lines is arranged at the right side. Numerical data of the so-called Strehl ratio is displayed at the sides of those. The drawing of the PSF shown on the plane is normalized by the Strehl ratio and is displayed.

The appearances of Landolt's rings corresponding to several kinds of different visual acuity, which are presumed to be observed based on the measured optical characteristics, together with numerals of visual acuity values, are displayed at the lower side. Since these three kinds of display modes can be observed at the same time, a quick and accurate judgment becomes possible.

FIFTEENTH DISPLAY EXAMPLE

Figure 28:
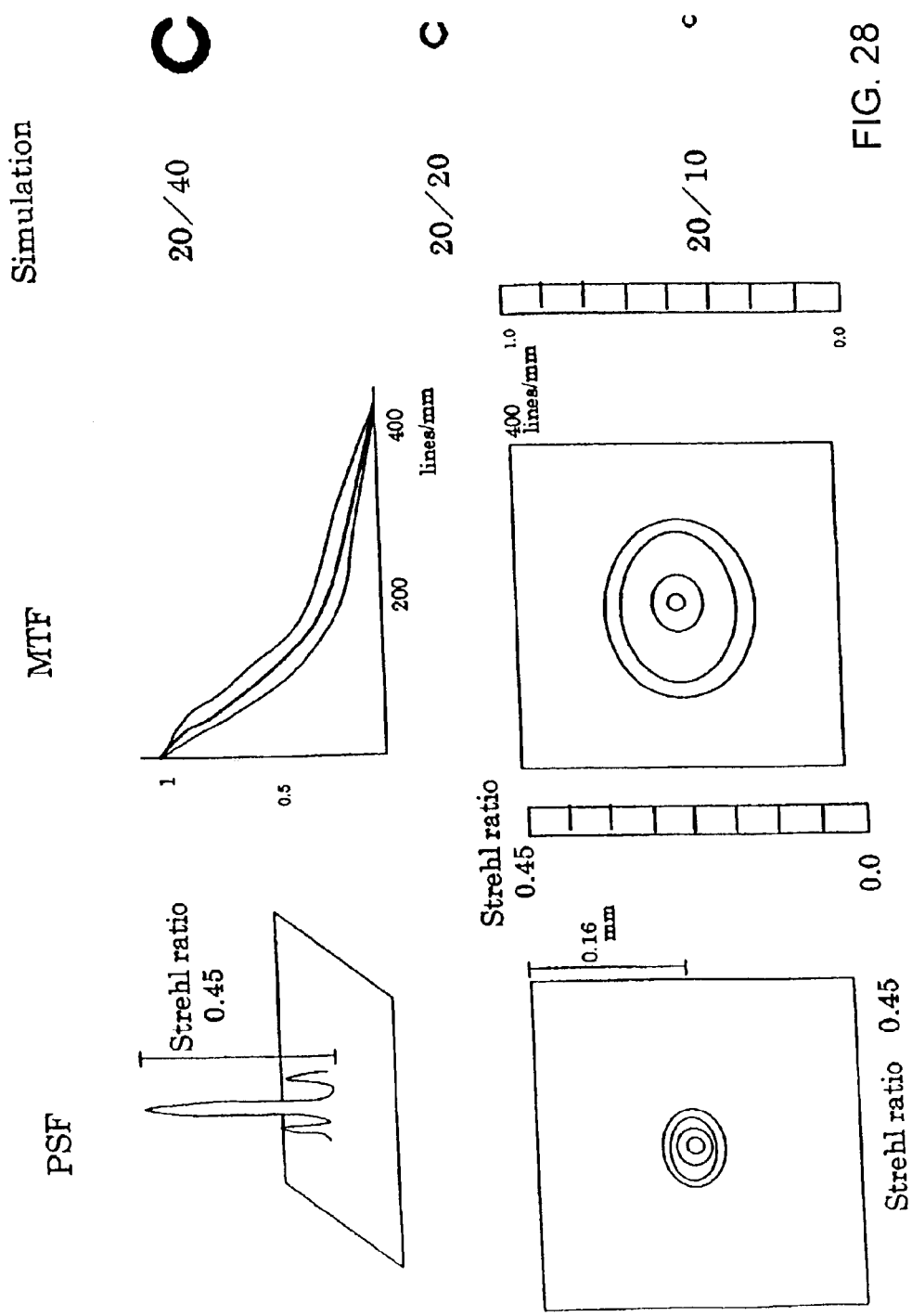
FIG. 28 is an explanatory view showing a fifteenth display example graphically displayed on the display section 230.

FIG. 28 is an explanatory view showing a fifteenth display example graphically displayed on the display section 230.

A display mode will be described which can be displayed instead of the MTF display shown in FIG. 5 as the first display example or shown in FIG. 8 as the second display example, or in addition to this.

In the left side of FIG. 28, a drawing in which PSF indicating the optical characteristics of the eye 60 to be measured is shown by contour lines on a plane is arranged at the lower stage, and a drawing in which the PSF is three-dimensionally shown is arranged at the upper stage. The drawing of the PSF shown here on the plane is normalized by the Strehl ratio and is displayed. Further, in the right side, a drawing in which MTF indicating the optical characteristics of the eye 60 to be measured is shown two-dimensionally or in a section of a predetermined axial direction, or in a section of one of or plural (for example, three) sections of the x direction, y direction, and its average, is arranged at the upper stage, and a drawing in which it is shown by contour lines on the plain is arranged at the lower stage.

Numerical data of the so-called Strehl ratio is displayed at the sides of those. Appearances of Landolt's rings corresponding to several different kinds of visual acuity, which are presumed to be observed based on the measured optical characteristics, together with numerals of visual acuity values, are displayed at the rightmost side. Since these three kinds of display modes can be observed at the same time, a quick and accurate judgment becomes possible.

As stated above, in the optical characteristic measuring apparatus 100 of this embodiment, for example, the measurement data (measured results) obtained under plural conditions, image data and/or numerical value data corresponding to the measured results can be graphically displayed on the display section 230 collectively or selectively as the need arises. Incidentally, in all the Hartmann images and aberration drawings shown in the foregoing respective display examples, an anterior eye image, a spot center-of-gravity position capable of being used for analysis, and a reference lattice point corresponding to the spot center-of-gravity position can be respectively overlapped and displayed.

INDUSTRIAL APPLICABILITY

According to the present invention, as described above, measurement data (measured results) obtained under plural conditions, image data and/or numerical value data corresponding to the measured results can be collectively or selectively displayed.

Besides, according to the invention, with respect to the whole of the eye to be measured, the cornea, and the internal, measurement data (measured results), image data and/or numerical value data corresponding to the measured results can be collectively or selectively displayed.

What is claimed is:

1. An optical characteristic measuring apparatus, comprising:
    an illumination optical system including a light source section for applying a light flux of a predetermined pattern to an eye to be measured and forming substantially a point light source as a predetermined pattern on an eyeground of the eye to be measured;
    a light receiving optical system including a light receiving section for receiving reflected light from the eye to be measured and a Hartmann plate for dividing the reflected light from the eye to be measured into plural light fluxes;
    a calculation section for calculating, based on received optical signals corresponding to a Hartmann image indicating measurement data from the light receiving section, optical characteristics of the eye to be measured in a form of refraction or power as the measurement data; and
    a display section for graphically displaying an optical refractive power distribution or a power map of the eye to be measured in accordance with the measurement data obtained by the calculation section.

2. An optical characteristic measuring apparatus according to claim 1, wherein
    the calculation section calculates the optical characteristics under plural conditions for the graphic display based on the received optical signals, and
    the display section graphically displays the measurement data based on the received optical signals under the plural measurement conditions and the optical characteristics obtained by the calculation section.

3. An optical characteristic measuring apparatus according to claim 2, wherein
    the plural measurement conditions are determined by that at least the received optical signals corresponding to a change of a measurement range at the eye to be measured, and
    the display section graphically displays the measurement data based on the received optical signals and the optical characteristics obtained by the calculation section in accordance with a manipulation of a measurer and corresponding to the measurement range under the plural measurement conditions.

4. An optical characteristic measuring apparatus according to claim 3, wherein a reference lattice point included in the Hartmann image is overlaid and displayed in an aberration drawing.

5. An optical characteristic measuring apparatus according to claim 1, wherein the display section selectively displays graphic display of, in accordance with a manipulation of a measurer, the measurement data based on the received optical signals under the plural measurement conditions, or the optical characteristics obtained by the calculation section.

6. An optical characteristic measuring apparatus according to claim 1, further comprising a pointing device, such as a mouse, for a measurer to perform a manipulation,
    wherein the calculation section further calculates numerical data indicating the optical characteristics under plural conditions,
    the display section further displays the numerical data under the plural conditions as a list, and
    wherein, in a case where the measurer selects the numerical value data under one of the measurement conditions on the display of the display section, the measurement data corresponding to the selected numerical data, and the optical characteristics based on the measurement data are graphically displayed.

7. An optical characteristic measuring apparatus according to claim 1, wherein the calculation section performs an operation in such a manner that plural conditions are a photopic time and a scotopic time, a measurement region included in the eye to be measured is made a region corresponding to a size of a pupil at the photopic time or the scotopic time, and the optical characteristics are graphically displayed.

8. An optical characteristic measuring apparatus according to claim 1, wherein the graphic display is one of an aberration drawing expressing an aberration two-dimensionally or three-dimensionally, a drawing showing MTF two-dimensionally or in a section of a predetermined axial direction, or in one or plural of sections of an x direction, a y direction and its average, a drawing showing PSF two-dimensionally or three-dimensionally, and Landolt's rings corresponding to several kinds of visual acuity.

9. An optical characteristic measuring apparatus according to claim 1, wherein
    the illumination optical system applies ring-shaped light fluxes of different diameters to a cornea of the eye to be measured,
    the light receiving optical system receives the reflected light from the cornea of the eye to be measured,
    the received optical signals from the light receiving section indicate a placido ring, and
    the graphic display of the optical characteristics indicates a shape of the cornea of the eye to be measured.

10. An optical characteristic measuring apparatus according to claim 1, wherein
    the light receiving optical system further comprises a second light receiving section for receiving an anterior eye image of the eye to be measured, and
    the display section causes the measured results to overlap with the anterior eye image and graphically displays them.

11. An optical characteristic measuring apparatus according to claim 1, wherein the display section indicates a center-of-gravity position as a basis of the optical characteristics of a Hartmann image or its displacement.

12. An optical characteristic measuring apparatus according to claim 1, wherein the display section displays an overlap of a reference lattice point and a Hartmann image.

13. An optical characteristic measuring apparatus according to claim 1, wherein the calculation section calculates internal aberrations based on the optical characteristics of the eye to be measured and optical characteristics of a cornea, and the display section displays the internal aberrations.

14. An optical characteristic measuring apparatus according to claim 1, wherein the calculation section calculates a corneal aberration, and the display section displays the corneal aberration.

15. An optical characteristic measuring apparatus according to claim 1, wherein the calculation section calculates Zernike coefficients, and calculates, based on the Zernike coefficients, all aberrations or high order aberrations of the eye to be measured, and the display section displays all the aberrations or the high order aberrations of the eye to be measured obtained by the calculation section.

16. An optical characteristic measuring apparatus according to claim 1, wherein a Hartmann image of a photographed raw image, all aberrations of the eye to be measured including at least a second-order aberration, and high order aberrations including third-order and higher aberrations are displayed in the display section.

17. An optical characteristic measuring apparatus according to claim 16, wherein a point strength distribution calculated from the high order aberrations or all aberrations of at least second-order and higher aberrations is displayed in the display section.

18. An optical characteristic measuring apparatus according to claim 1, wherein the Hartmann image, all high order aberrations including third-order and higher aberrations, and the respective high order aberrations included in all the high order aberrations are divided into symmetrical aberrations and asymmetrical aberrations and are displayed in the display section.

19. An optical characteristic measuring apparatus according to claim 1, wherein the Hartmann image, all high order aberrations including third-order and higher aberrations, and the respective high order aberrations included in all the high order aberrations are individually displayed in the display section.

20. An optical characteristic measuring apparatus according to claim 1, wherein a placido image, all aberrations of the eye to be measured including at least second-order and higher aberrations, and high order aberrations including third-order and higher aberrations are displayed in the display section.

21. An optical characteristic measuring apparatus according to claim 20, wherein the display section graphically displays, on a same screen, the refractive power distribution or the power map of the eyeball of the eye to be measured and the refractive power distribution or the power map of the cornea of the eye to be measured.

22. An optical characteristic measuring apparatus according to claim 21, wherein the plural refractive power distributions or power forms are power forms of the cornea, and are one of a corneal axial power map, an instantaneous power map, and a refractive power map.

23. An optical characteristic measuring apparatus according to claim 20, wherein the display section displays and switches, on a same screen, the refractive power distribution or the power map of the eyeball of the eye to be measured and the refractive power distribution or the power map of the cornea of the eye to be measured, which are graphically displayed.

24. An optical characteristic measuring apparatus according to claim 1, wherein the illumination optical system applies ring-shaped light fluxes of different diameters to a cornea of the eye to be measured, the light receiving optical system receives the reflected light from the cornea of the eye to be measured, the received optical signals from the light receiving section indicate a placido ring image, and the display section graphically displays a refractive power distribution or a power map of the cornea of the eye to be measured.

25. An optical characteristic measuring apparatus according to claim 1, wherein the calculation section further calculates optical characteristics of the eye as the measurement data in an aberration form, and the display section displays the refractive power distribution or power of the eyeball of the eye to be measured in a numerical value form and an aberration coefficient form.

26. An optical characteristic measuring apparatus according to claim 1, wherein the calculation section further calculates optical characteristics of the eye as the measurement data in an aberration form, and the display section graphically displays the refractive power distribution map form of the eyeball of the eye to be measured or a power map form, and an aberration map form.

* * * * *